US012600790B2

(12) United States Patent
Swanson et al.

(10) Patent No.: US 12,600,790 B2
(45) Date of Patent: Apr. 14, 2026

(54) VARIANT ANTIBODY THAT BINDS CD38

(71) Applicant: Sorrento Therapeutics, Inc., San Diego, CA (US)

(72) Inventors: Barbara A. Swanson, San Diego, CA (US); Heyue Zhou, San Diego, CA (US); Jian Cao, San Diego, CA (US)

(73) Assignee: Vivasor, Inc., San Diego, CA (US)

( * ) Notice: Subject to any disclaimer, the term of this patent is extended or adjusted under 35 U.S.C. 154(b) by 1343 days.

(21) Appl. No.: 17/127,766

(22) Filed: Dec. 18, 2020

(65) Prior Publication Data

US 2021/0130484 A1 May 6, 2021

Related U.S. Application Data

(63) Continuation of application No. PCT/US2019/021417, filed on Mar. 8, 2019.

(60) Provisional application No. 62/687,695, filed on Jun. 20, 2018.

(51) Int. Cl.

| | |
|---|---|
| *C07K 16/00* | (2006.01) |
| *A61K 39/00* | (2006.01) |
| *A61K 39/395* | (2006.01) |
| *C07K 16/28* | (2006.01) |
| *C07K 16/46* | (2006.01) |
| *C12N 5/00* | (2006.01) |
| *C12N 5/08* | (2006.01) |
| *C12N 15/00* | (2006.01) |
| *C12N 15/09* | (2006.01) |
| *C12N 15/53* | (2006.01) |

(52) U.S. Cl.
CPC .......... *C07K 16/2878* (2013.01); *A61K 39/00* (2013.01); *C07K 2317/21* (2013.01); *C07K 2317/55* (2013.01); *C12N 5/00* (2013.01); *C12N 15/00* (2013.01)

(58) Field of Classification Search
CPC ............ C07K 16/2878; C07K 2317/21; C07K 2317/55; C07K 2317/565; C07K 2317/24; C07K 2317/92; C07K 16/2896; A61K 2039/505
See application file for complete search history.

(56) References Cited

U.S. PATENT DOCUMENTS

| | | | | |
|---|---|---|---|---|
| 10,059,774 | B2 * | 8/2018 | Zhou | A61P 35/00 |
| 10,800,852 | B2 * | 10/2020 | Zhou | A61K 39/395 |
| 11,191,842 | B2 * | 12/2021 | Yang | A61K 9/0024 |
| 11,760,806 | B2 * | 9/2023 | Zhang | C07K 16/2896 |
| | | | | 530/387.3 |
| 2009/0252733 | A1 | 10/2009 | Tesar | |
| 2016/0297888 | A1 * | 10/2016 | Zhou | A61K 39/39558 |
| 2018/0360985 | A1 * | 12/2018 | Zhu | A61K 31/704 |
| 2020/0399393 | A1 * | 12/2020 | Ji | A61K 40/4222 |
| 2020/0399395 | A1 * | 12/2020 | Zhou | A61P 35/02 |
| 2022/0118105 | A1 * | 4/2022 | Zhu | A61K 47/6817 |

FOREIGN PATENT DOCUMENTS

| | | |
|---|---|---|
| JP | 2018513149 A | 5/2018 |
| WO | 2005103083 A2 | 11/2005 |
| WO | 2016164656 A1 | 10/2016 |
| WO | 2016164669 A2 | 10/2016 |
| WO | 2018235024 A1 | 12/2018 |

OTHER PUBLICATIONS

Clancy, S., & Brown, W. (2008). Translation: DNA to mRNA until Protein. Nature Education, 1(1), 101. (Year: 2008).*
Atanackovic, D. et al, Immunotherapies targeting CD38 in Multiple Myeloma, 2016, Oncoimmunology, vol. 5, No. 11, e1217374 (11 pages). (Year: 2016).*
Ding, Bei Bei, et al, Development of a Genetically-Engineered Allogeneic Anti-CD38 T Cell Therapy Utilizing a Novel Antigen Receptor Structure, 2019, Blood , vol. 134, pp. 1-2. (Year: 2019).*
Solomon, A. et al had disclosed in their publication titled, Structural and functional properties of human lambda-light-chain variable-region subgroups, 1995, Clinical and Diagnostic Laboratory Immunology, vol. 2, No. 4, pp. 387-394 (Year: 1995).*
Daniels, R.W. et al, Expression of multiple transgenes from a single construct using viral 2A peptides in Drosophila, 2014, PLoS One, vol. 9, No. 6, e100637, pp. 1-10 (Year: 2014).*
Extended European Search Report corresponding to European Patent Application No. 19822721.7, mailed Feb. 10, 2022, 7 pages.
Ausiello et al. 2000, "Functional topography of discrete domains of human CD38", Tissue Antigens, 56:539-547.
Dagher et al., 1998, "c-Kit and CD38 are expressed by long-term reconstituting hematopoietic cells present in the murine yolk sac", Biol. Blood Marrow Transplant, 4:69-74.
Deaglio et al., 2003, "CD38 is a signaling molecule in B-cell chronic lymphocytic leukemia cells", Blood 102: 2146-2155.
Funaro et al., 1993, "Human CD38 is associated to distinct molecules which mediate transmembrane signaling in different lineages", Eur. J. Immunol., 23: 2407-2411.
International Search Report corresponding to International Patent Application No. PCT/US2019/021417, mailed May 24, 2019, 9 pages.
Kitanaka et al., 1997, "CD38 ligation in human B cell progenitors triggers tyrosine phosphorylation of CD19 and association of CD19 with lyn and phosphatidylinositol 3-kinase", J. Immunol., 159: 184-192.

(Continued)

*Primary Examiner* — Bridget E Bunner
*Assistant Examiner* — Regina M DeBerry
(74) *Attorney, Agent, or Firm* — McNeill PLLC

(57) ABSTRACT

The present disclosure provides anti-CD38 IgG class antibody having improved ability to be manufactured at higher yields compared to the parent antibody having the original wild type sequence. The present disclosure provides a mutated antibody light chain that reduces cleavage heterogeneity for improved production of a homogeneous population of antibody light chains.

19 Claims, 3 Drawing Sheets

Specification includes a Sequence Listing.

(56)                References Cited

OTHER PUBLICATIONS

Kitanaka et al., 1999, "CD38-Mediated Signaling Events in Murine Pro-B Cells Expressing Human CD38 With or Without Its Cytoplasmic Domain", J. Immunol., 162: 1952-1958.
Konopleva et al. 1998, "Ligation of Cell Surface CD38 Protein with Agonistic Monoclonal Antibody Induces a Cell Growth Signal in Myeloid Leukemia Cells", J. Immunol., 161:4702-4708.
Kumagai et al. 1995, "Ligation of CD38 suppresses human B lymphopoiesis", J. Exp. Med., 181:1101-1110.
Mallone et al., 2001, "Signaling through CD38 induces NK cell activation", Int. Immunol., 13: 397-409.
Morra et al. 1998, "CD38 is functionally dependent on the TCR/CD3 complex in human T cells", FASEB J., 12:581-592.
Oliver et al., 1997, "Mouse CD38 is down-regulated on germinal center B cells and mature plasma cells", J. Immunol., 158:108-1115.
Partida-Sanchez et al., 2001, "Cyclic ADP-ribose production by CD38 regulates intracellular calcium release, extracellular calcium influx and chemotaxis in neutrophils and is required for bacterial clearance in vivo", Nat. Med., 7:1209-1216.
Partida-Sanchez et al., 2004, "Regulation of Dendritic Cell Trafficking by the ADP-Ribosyl Cyclase CD38: Impact on the Development of Humoral Immunity", Immunity, 20: 279-291.

Randall et al., 1996, "Expression of murine CD38 defines a population of long-term reconstituting hematopoietic stem cells", Blood, 87:4057-4067.
Ridderstad and Tarlinton 1998, "Kinetics of Establishing the Memory B Cell Population as Revealed by CD38 Expression", J. Immunol., 160:4688-4695.
Stevenson et al., 1991, "Preliminary studies for an immunotherapeutic approach to the treatment of human myeloma using chimeric anti-CD38 antibody", Blood, 77:1071-1079.
Todisco et al. 2000, "CD38 ligation inhibits normal and leukemic myelopoiesis", Blood, 95:535-542.
Uckun, 1990, "Regulation of human B-cell ontogeny", Blood, 76:1908-1923.
Zilber et al., 2000, "CD38 expressed on human monocytes: A coaccessory molecule in the superantigen-induced proliferation", Proc. Natl. Acad. Sci. USA, 97: 2840-2845.
Zubiaur et al., 1997, "CD38 ligation results in activation of the Raf-1/mitogen-activated protein kinase and the CD3-zeta/zeta-associated protein-70 signaling pathways in Jurkat T lymphocytes.", J Immunol, 159: 193-205.
Zupo et al. 1994, "CD38 signaling by agonistic monoclonal antibody prevents apoptosis of human germinal center B cells", Eur. J. Immunol., 24:1218-1222.
Gibson et al., "N-terminal or signal peptide sequence engineering prevents truncation of human monoclonal antibody light chains," Biotechnol Bioeng. Sep. 2017; 114(9): 1970-1977.

* cited by examiner

SEQUENCE LISTING

<160> NUMBER OF SEQ ID NOS: 6

<210> SEQ ID NO 1
<211> LENGTH: 118
<212> TYPE: PRT
<213> ORGANISM: Artificial Sequence
<220> FEATURE:
<223> OTHER INFORMATION: Artificial antibody variable region

<400> SEQUENCE: 1

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asp
            20                  25                  30

-continued

```
Tyr Met Ser Trp Ile Arg Gln Ala Pro Gly Lys Gly Leu Glu Trp Val
        35                  40                  45

Ala Ser Val Ser Asn Gly Arg Pro Thr Thr Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Asp Trp Gly Gly Glu Phe Thr Asp Trp Gly Arg Gly Thr
                100                 105                 110

Leu Val Thr Val Ser Ser
        115

<210> SEQ ID NO 2
<211> LENGTH: 110
<212> TYPE: PRT
<213> ORGANISM: Artificial Sequence
<220> FEATURE:
<223> OTHER INFORMATION: Artificial antibody variable region

<400> SEQUENCE: 2

Gln Ala Gly Leu Thr Gln Pro Pro Ser Ala Ser Gly Thr Ser Gly Gln
1               5                   10                  15

Arg Val Thr Ile Ser Cys Ser Gly Ser Ser Ser Asn Ile Gly Ile Asn
                20                  25                  30

Phe Val Tyr Trp Tyr Gln His Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Asn Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Ser Gly Thr Lys Val Thr Val Leu
            100                 105                 110

<210> SEQ ID NO 3
<211> LENGTH: 110
<212> TYPE: PRT
<213> ORGANISM: Artificial Sequence
<220> FEATURE:
<223> OTHER INFORMATION: Artificial antibody variable region

<400> SEQUENCE: 3

Gln Ser Val Leu Thr Gln Pro Pro Ser Ala Ser Gly Thr Ser Gly Gln
1               5                   10                  15

Arg Val Thr Ile Ser Cys Ser Gly Ser Ser Ser Asn Ile Gly Ile Asn
                20                  25                  30

Phe Val Tyr Trp Tyr Gln His Leu Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Asn Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Tyr Val Phe Gly Ser Gly Thr Lys Val Thr Val Leu
```

-continued

```
              100           105           110

<210> SEQ ID NO 4
<211> LENGTH: 5
<212> TYPE: PRT
<213> ORGANISM: Artificial Sequence
<220> FEATURE:
<223> OTHER INFORMATION: Artificial antibody variable region subsegment

<400> SEQUENCE: 4

Gln Ala Gly Leu Thr
1               5

<210> SEQ ID NO 5
<211> LENGTH: 5
<212> TYPE: PRT
<213> ORGANISM: Artificial Sequence
<220> FEATURE:
<223> OTHER INFORMATION: Artificial antibody variable region subsegment

<400> SEQUENCE: 5

Gln Ser Val Leu Thr
1               5

<210> SEQ ID NO 6
<211> LENGTH: 5
<212> TYPE: PRT
<213> ORGANISM: Artificial Sequence
<220> FEATURE:
<223> OTHER INFORMATION: Artificial antibody variable region subsegment

<400> SEQUENCE: 6

Gln Ser Ala Leu Thr
1               5
```

VARIANT ANTIBODY THAT BINDS CD38

This application is a continuation of International Patent Application No. PCT/US2019/021417, filed Mar. 8, 2019, which claims the benefit of priority to U.S. provisional application No. 62/687,695, filed Jun. 20, 2018, the contents of each of which are incorporated herein by reference in their entirety.

Throughout this application various publications, patents, and/or patent applications are referenced. The disclosures of the publications, patents and/or patent applications are hereby incorporated by reference in their entireties into this application in order to more fully describe the state of the art to which this disclosure pertains. To the extent any material incorporated by reference conflicts with the express content of this application, the express content controls.

SEQUENCE LISTING

The present application is filed with a Sequence Listing in electronic format. The Sequence Listing is provided as a file entitled "2019-03-08_01223-0013-00PCT_SE-Q_LIST_ST25" created on Mar. 8, 2019, which is 4,096 bytes in size. The information in the electronic format of the sequence listing is incorporated herein by reference in its entirety.

TECHNICAL FIELD

The present disclosure provides an anti-CD38 IgG class antibody having a variant light chain relative to the wild-type sequence. Disclosed antibodies can have an improved ability to be manufactured at higher yields compared to the wild-type antibody and/or reduced cleavage heterogeneity, which can improve homogeneity of antibody light chains.

INTRODUCTION AND SUMMARY

CD38 is a 45 kD type II transmembrane glycoprotein with a long C-terminal extracellular domain and a short N-terminal cytoplasmic domain. The CD38 protein is a bifunctional ectoenzyme that can catalyze the conversion of $NAD^+$ into cyclic ADP-ribose (cADPR) and also hydrolyze cADPR into ADP-ribose. During ontogeny, CD38 appears on $CD34^+$ committed stem cells and lineage-committed progenitors of lymphoid, erythroid and myeloid cells. CD38 expression persists mostly in the lymphoid lineage with varying expression levels at different stages of T and B cell development.

CD38 is upregulated in many hematopoietic malignancies and in cell lines derived from various hematopoietic malignancies, including non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). On the other hand, most primitive pluripotent stem cells of the hematopoietic system are CD38⁻. CD38 expression in hematopoietic malignancies and its correlation with disease progression makes CD38 an attractive target for anti-CD38 antibody therapy.

CD38 has been reported to be involved in $Ca^{2+}$ mobilization (Morra et al., 1998, FASEB J., 12: 581-592; Zilber et al., 2000, Proc. Natl. Acad. Sci. USA, 97: 2840-2845) and in the signal transduction through tyrosine phosphorylation of numerous signaling molecules, including phospholipase C-γ, ZAP-70, syk, and c-cbl, in lymphoid and myeloid cells or cell lines (Funaro et al., 1993, Eur. J. Immunol., 23: 2407-2411; Morra et al., 1998, FASEB J., 12: 581-592; Funaro et al., 1990, J Immunol, 145: 2390-2396; Zubiaur et al., 1997, J Immunol, 159: 193-205; Deaglio et al., 2003, Blood 102: 2146-2155; Todisco et al., 2000, Blood, 95: 535-542; Konopleva et al., 1998, J. Immunol., 161: 4702-4708; Zilber et al., 2000, Proc. Natl. Acad. Sci. USA, 97: 2840-2845; Kitanaka et al., 1997, J. Immunol., 159: 184-192; Kitanaka et al., 1999, J. Immunol., 162: 1952-1958; Mallone et al., 2001, Int. Immunol., 13: 397-409). CD38 was proposed to be an important signaling molecule in the maturation and activation of lymphoid and myeloid cells during their normal development.

Evidence for the function of CD38 comes from CD38⁻/⁻ knockout mice, which have a defect in their innate immunity and a reduced T-cell dependent humoral response due to a defect in dendritic cell migration (Partida-Sanchez et al., 2004, Immunity, 20: 279-291; Partida-Sanchez et al., 2001, Nat. Med., 7:1209-1216). Nevertheless, it is not clear if the CD38 function in mice is identical to that in humans since the CD38 expression pattern during hematopoiesis differs greatly between human and mouse: a) unlike immature progenitor stem cells in humans, similar progenitor stem cells in mice express a high level of CD38 (Randall et al., 1996, Blood, 87:4057-4067; Dagher et al., 1998, Biol. Blood Marrow Transplant, 4:69-74), b) while during the human B cell development, high levels of CD38 expression are found in germinal center B cells and plasma cells (Uckun, 1990, Blood, 76:1908-1923; Kumagai et al., 1995, J. Exp. Med., 181:1101-1110), in the mouse, the CD38 expression levels in the corresponding cells are low (Oliver et al., 1997, J. Immunol., 158:108-1115; Ridderstad and Tarlinton 1998, J. Immunol., 160:4688-4695).

Several anti-human CD38 antibodies with different proliferative properties on various tumor cells and cell lines have been described in the literature. For example, a chimeric OKT10 antibody with mouse Fab and human IgG1 Fc mediates antibody-dependent cell-mediated cytotoxicity (ADCC) very efficiently against lymphoma cells in the presence of peripheral blood mononuclear effector cells from either MM patients or normal individuals (Stevenson et al., 1991, Blood, 77:1071-1079). A CDR-grafted humanized version of the anti-CD38 antibody AT13/5 has been shown to have potent ADCC activity against CD38-positive cell lines. Human monoclonal anti-CD38 antibodies have been shown to mediate the in vitro killing of CD38-positive cell lines by ADCC and/or complement-dependent cytotoxicity (CDC), and to delay the tumor growth in SCID mice bearing MM cell line RPMI-8226 (WO2005/103083 A2). On the other hand, several anti-CD38 antibodies, IB4, SUN-4B7, and OKT10, but not IB6, AT1, or AT2, induced the proliferation of peripheral blood mononuclear cells (PBMC) from normal individuals (Ausiello et al. 2000, Tissue Antigens, 56:539-547).

Some of the antibodies of the prior art have been reported to be able to trigger apoptosis in CD38⁺ B cells in a stroma cell-dependent or stroma-derived cytokine-dependent manner. An agonistic anti-CD38 antibody (IB4) has been reported to prevent apoptosis of human germinal center (GC) B cells (Zupo et al. 1994, Eur. J. Immunol., 24:1218-1222), and to induce proliferation of KG-1 and HL-60 AML cells (Konopleva et al. 1998, J. Immunol., 161:4702-4708), but induces apoptosis in Jurkat T lymphoblastic cells (Morra et al. 1998, FASEB J., 12:581-592). Another anti-CD38 antibody, T16, induced apoptosis of immature lymphoid cells and leukemic lymphoblast cells from an ALL patient (Kumagai et al. 1995, J. Exp. Med., 181:1101-1110), and of leukemic myeloblast cells from AML patients (Todisco et al. 2000, *Blood*, 95:535-542), but T16 induced apoptosis only in the presence of stroma cells or stroma-derived cytokines (IL-7, IL-3, stem cell factor).

Therefore, antibody drug conjugates (ADCs), targeted with anti-CD38 antibodies, offer the promise and potential of delivering potent anti-tumor activity with the advantage of reduced side effects. Thus, there remains a need in the art for effective treatments based on CD38, particularly anti-CD38 antibodies. The present disclosure provides variant antibody sequences that differ from the fully human wild type sequence. Disclosed variant antibodies can be manufactured in much higher yield and/or provide improved light chain homogeneity.

The present disclosure provides an antigen binding protein that binds CD38, comprising a heavy chain variable region and a light chain variable region, wherein the heavy chain variable region comprises the sequence of SEQ ID NO: 1 and the light chain comprises the sequence of SEQ ID NO: 3. Such an antigen binding protein may be, for example, a single chain antibody, which may be fully human. The present disclosure provides a fully human antibody of an IgG class or antibody Fab fragment, comprising a heavy chain comprising a heavy chain variable region having an amino acid sequence of SEQ ID NO:1, and a light chain comprising a light chain variable region having an amino acid sequence of SEQ ID NO:3. The present disclosure provides a nucleic acid encoding an antibody light chain comprising a light chain variable region having an amino acid sequence of SEQ ID NO:3, which may be in combination with or further comprise a nucleic acid encoding an antibody heavy chain which comprises the amino acid sequence of SEQ ID NO:1.

The present disclosure also provides a population of a variant antibody of an IgG class, and methods for making the population of the variant antibody. The population of the variant antibody comprises two or more of the variant antibody (e.g., a plurality of the variant antibody). Individual variant antibodies in the population comprise immunoglobulins each having two antibody heavy chains and two antibody light chains, where the light chains have a mutant sequence. The light chain mutant sequence reduces cleavage heterogeneity during antibody preparation. For example, a population of the variant antibody can be prepared by host cell expression of a recombinant antibody heavy chain and light chain. The light chain variant sequence can reduce the level of polypeptide length heterogeneity and the level of amino acid sequence heterogeneity by about 40-55% during antibody preparation, thereby reducing heterogeneity in a preparation of the variant antibody.

The present disclosure provides a population of a variant antibody of an IgG class, which exhibits a reduced level of polypeptide length heterogeneity and a reduced level of amino acid sequence heterogeneity compared to a population of a parent wild type antibody of an IgG class which exhibits a higher level of polypeptide length heterogeneity and a higher level of amino acid sequence heterogeneity. Individual antibodies in the population of the variant antibody comprise a heavy chain having a wild type amino acid sequence and a light chain having a mutant amino acid sequence. The variant amino acid sequence of the light chain can reduce the level of the polypeptide length heterogeneity and reduces the level of amino acid sequence heterogeneity in the population of variant antibody by about 40-55%.

In one embodiment, the population of the variant antibody comprises individual variant sequence antibodies having a heavy chain which comprises a heavy chain variable region having the wild type amino acid sequence of SEQ ID NO:1, and the individual variant antibodies having a light chain which comprise a light chain variable region having the mutant amino acid sequence of SEQ ID NO:3.

In one embodiment, the population of the variant antibody binds a CD38 epitope.

In one embodiment, the population of the variant antibody comprises fully human antibodies.

In one embodiment, the individual parent wild type antibodies in the population of the parent wild type antibody comprise a light chain having the wild type amino acid sequence of which about 40-55% exhibit polypeptide length heterogeneity and amino acid sequence heterogeneity.

In one embodiment, the individual variant antibodies in the population of the variant antibody comprise a light chain having the mutant amino acid sequence of which about 85-99%, 85-100%, 90-99%, or 90-100% exhibit polypeptide length homogeneity and amino acid sequence homogeneity. Homogeneity may be quantified as the percentage of members of a population (e.g., of antibody light chains) that have the length and/or sequence of the plurality or majority species (e.g., light chains comprising a variable region having the sequence of SEQ ID NO:3) in the population.

In one embodiment, the population of the variant antibody of IgG class binds to the CD38 epitope, and exhibits the reduced level of polypeptide length heterogeneity and the reduced level of sequence heterogeneity compared to the population of the parent wild type antibody of IgG class which exhibits the higher level of polypeptide length heterogeneity and the higher level of sequence heterogeneity, wherein individual antibodies in the variant sequence population comprise a heavy chain having a wild type amino acid sequence and a light chain having a mutant amino acid sequence, wherein the heavy chain of the individual variant antibodies comprise a heavy chain variable region having the wild type amino acid sequence of SEQ ID NO:1, wherein the light chain of the individual variant antibodies comprise a light chain variable region having the mutant amino acid sequence of SEQ ID NO:3, and wherein the mutant amino acid sequence of the light chain reduces the level of the polypeptide length heterogeneity and the level of sequence heterogeneity by about 40-55%.

The present disclosure provides a population of a fully human IgG class antibody comprising a heavy chain having the heavy chain variable region wild type amino acid sequence of SEQ ID NO:1 and a light chain having the light chain variable region mutant amino acid sequence of SEQ ID NO:3.

The present disclosure provides a population of a fully human Fab fragment comprising a heavy chain having the heavy chain variable region wild type amino acid sequence of SEQ ID NO:1 and a light chain having the light chain variable region mutant amino acid sequence of SEQ ID NO:3.

The present disclosure provides a population of an antigen binding protein (e.g., a single chain antibody, which may be fully human) comprising a heavy chain variable region wild type amino acid sequence of SEQ ID NO:1 and a light chain variable region mutant amino acid sequence of SEQ ID NO:3. In one embodiment, the single chain antibody comprises a heavy chain variable region and a light chain variable region joined together by a peptide linker.

The present disclosure provides a population of an antigen binding protein (e.g., a fully human IgG class antibody) comprising a heavy chain having the heavy chain variable region wild type amino acid sequence of SEQ ID NO:1, and a light chain comprising the amino acid sequence of SEQ ID NO:2 having two point mutations near the N-terminal end, specifically alanine at position 2 is replaced with serine, and glycine at position 3 is replaced with alanine. In one embodiment, the N-terminal end of the mutant light chain contains the amino acid sequence QSALT (SEQ ID NO: 6).

The present disclosure provides a population of a variant antibody light chain which exhibits a reduced level of polypeptide length heterogeneity and a reduced level of amino acid sequence heterogeneity compared to a population of a parent wild type antibody light chain which exhibits a higher level of polypeptide length and a higher level of amino acid sequence heterogeneity. Individual antibody light chains in the population of the variant antibody light chain comprise a light chain variable region having the mutant amino acid sequence of SEQ ID NO:3.

In one embodiment, the individual variant sequence light chains in the population comprise a fully human antibody light chain.

In one embodiment, individual parent wild type sequence antibody light chains in the population of the parent wild type antibody comprise the light chain variable region having the parent wild type amino acid sequence of which about 40-55%% exhibit polypeptide length heterogeneity and amino acid sequence heterogeneity.

In one embodiment, the individual variant antibodies in the population of the variant antibody comprise a light chain having the mutant amino acid sequence of which about 85-99%, 85-100%, 90-99%, or 90-100% exhibit polypeptide length homogeneity and amino acid sequence homogeneity.

In one embodiment, the variant antibody light chain of IgG class exhibits the reduced level of polypeptide length heterogeneity and the reduced level of amino acid sequence heterogeneity compared to the population of the parent wild type antibody having the higher level of polypeptide length heterogeneity and the higher level of amino acid sequence heterogeneity. Individual antibody light chains in the population of the variant antibody light chain comprise a comprise a light chain variable region having the mutant amino acid sequence of SEQ ID NO:3, and wherein the mutant amino acid sequence of the light chain reduces the level of the polypeptide length heterogeneity and the level of amino acid sequence heterogeneity by about 40-55%.

In one embodiment, a fully human Fab fragment comprises a light chain having a light chain variable region mutant amino acid sequence of SEQ ID NO:3.

In one embodiment, a single chain fully human antibody comprises a light chain variable region having the amino acid sequence of SEQ ID NO:3.

The present disclosure provides a fully human variant antibody of an IgG class that bind a CD38 epitope, comprising a heavy chain having a heavy chain variable region having a wild type amino acid sequence of SEQ ID NO:1, and a light chain having a light chain variable region having a mutant amino acid sequence of SEQ ID NO:3.

The present disclosure provides a fully human antibody Fab fragment that binds a CD38 epitope, comprising a heavy chain having a heavy chain variable region having a wild type amino acid sequence of SEQ ID NO:1, and a light chain having a light chain variable region having a mutant amino acid sequence of SEQ ID NO:3.

The present disclosure provides an antigen binding protein (e.g., a single chain antibody, which may be fully human) that binds a CD38 epitope, comprising a heavy chain having a heavy chain variable region having a wild type amino acid sequence of SEQ ID NO:1, and a light chain having a light chain variable region having a mutant amino acid sequence of SEQ ID NO:3. In one embodiment, the single chain antibody comprises a heavy chain variable region and a light chain variable region joined together by a peptide linker.

The present disclosure provides a pharmaceutical composition comprising a pharmaceutically-acceptable excipient and a fully human antibody of IgG class comprising a heavy chain having a heavy chain variable region wild type amino acid sequence of SEQ ID NO:1 and a light chain having a light chain variable region mutant amino acid sequence of SEQ ID NO:3.

The present disclosure provides a pharmaceutical composition comprising a pharmaceutically-acceptable excipient and a fully human Fab fragment comprising a heavy chain having a heavy chain variable region wild type amino acid sequence of SEQ ID NO:1 and a light chain having a light chain variable region mutant amino acid sequence of SEQ ID NO:3.

The present disclosure provides a pharmaceutical composition comprising a pharmaceutically-acceptable excipient and an antigen binding protein (e.g., a single chain antibody, which may be fully human) comprising a heavy chain having a heavy chain variable region wild type amino acid sequence of SEQ ID NO:1 and a light chain having a light chain variable region mutant amino acid sequence of SEQ ID NO:3.

The present disclosure provides a nucleic acid encoding a light chain disclosed herein. The present disclosure provides a nucleic acid encoding an antibody light chain comprising a light chain variable region amino acid sequence of SEQ ID NO:3. In one embodiment, the nucleic acid further comprises a nucleic acid encoding an antibody heavy chain which comprises a heavy chain variable region wild type amino acid sequence of SEQ ID NO:1. In one embodiment, the nucleic acid encodes a fully human IgG class antibody. In one embodiment, the nucleic acid encodes an antigen binding protein (e.g., a single chain antibody, which may be fully human).

The present disclosure provides a nucleic acid encoding a Fab fragment having a light chain variable region mutant amino acid sequence of SEQ ID NO:3. In one embodiment, the nucleic acid encodes a Fab fragment which also includes an antibody heavy chain. In one embodiment, the nucleic acid further comprises a nucleic acid encoding an antibody heavy chain which comprises a heavy chain variable region wild type amino acid sequence of SEQ ID NO:1.

The present disclosure provides a nucleic acid encoding a single chain antibody having a light chain variable region mutant amino acid sequence of SEQ ID NO:3. In one embodiment, the nucleic acid encodes a single chain antibody which also includes an antibody heavy chain. In one embodiment, the nucleic acid further comprises a nucleic acid encoding an antibody heavy chain which comprises a heavy chain variable region wild type amino acid sequence of SEQ ID NO:1.

The present disclosure provides an expression vector operably linked to a nucleic acid disclosed herein, e.g., encoding an antibody light chain having a light chain variable region mutant amino acid sequence of SEQ ID NO:3. In one embodiment, the vector is further operably linked to a nucleic acid encoding an antibody heavy chain which comprises a heavy chain variable region wild type amino acid sequence of SEQ ID NO:1. In one embodiment, the expression vector is operably linked to one or more nucleic acids that encode a fully human IgG class antibody.

The present disclosure provides an expression vector operably linked to a nucleic acid encoding a Fab fragment having a light chain variable region mutant amino acid sequence of SEQ ID NO:3. In one embodiment, the vector encodes a Fab fragment which also includes an antibody heavy chain. In one embodiment, the vector is further operably linked to a nucleic acid encoding an antibody heavy chain which comprises a heavy chain variable region wild type amino acid sequence of SEQ ID NO:1.

The present disclosure provides an expression vector operably linked to a nucleic acid encoding an antigen binding protein (e.g., a single chain antibody, which may be fully human) having a light chain variable region mutant amino acid sequence of SEQ ID NO:3. In one embodiment, the vector encodes a single chain antibody which also includes an antibody heavy chain. In one embodiment, the vector is further operably linked to a nucleic acid encoding an antibody heavy chain which comprises a heavy chain variable region wild type amino acid sequence of SEQ ID NO:1.

The present disclosure provides a host cell comprising a nucleic acid disclosed herein encoding an antibody light chain. The present disclosure provides a host cell harboring an expression vector operably linked to a nucleic acid encoding an antibody light chain having a light chain variable region mutant amino acid sequence of SEQ ID NO:3. In one embodiment, the vector harbored by the host cell is further operably linked to a nucleic acid encoding an antibody heavy chain which comprises a heavy chain variable region wild type amino acid sequence of SEQ ID NO:1. In one embodiment, the host cell harbors a second expression vector which is operably linked to a nucleic acid encoding an antibody heavy chain which comprises a heavy chain variable region wild type amino acid sequence of SEQ ID NO:1. In one embodiment, the host cell expressed the antibody light chain and heavy chain. In one embodiment, the host cell expresses a fully human IgG class antibody having a light and heavy chain.

The present disclosure provides a host cell harboring an expression vector operably linked to a nucleic acid encoding a Fab fragment having a light chain variable region mutant amino acid sequence of SEQ ID NO:3. In one embodiment, the vector harbored by the host cell is further operably linked to a nucleic acid encoding a Fab fragment which comprises a heavy chain variable region wild type amino acid sequence of SEQ ID NO:1. In one embodiment, the host cell harbors a second expression vector which is operably linked to a nucleic acid encoding a Fab fragment having an antibody heavy chain which comprises a heavy chain variable region wild type amino acid sequence of SEQ ID NO:1. In one embodiment, the host cell expresses a fully human Fab fragment having a light and heavy chain.

The present disclosure provides a host cell harboring an expression vector operably linked to a nucleic acid encoding an antigen binding protein (e.g., a single chain antibody, which may be fully human) having a light chain variable region mutant amino acid sequence of SEQ ID NO:3. In one embodiment, the vector harbored by the host cell is further operably linked to a nucleic acid encoding a single chain antibody which comprises a heavy chain variable region wild type amino acid sequence of SEQ ID NO:1. In one embodiment, the host cell expresses an antigen binding protein (e.g., a single chain antibody, which may be fully human) having a light chain variable region and a heavy chain variable region.

The present disclosure provides a method for preparing a fully human antibody light chain, comprising: culturing a population of the host cell under conditions suitable for expressing the antibody light chain, wherein individual host cells in the population harbor an expression vector operably linked to a nucleic acid encoding an antibody light chain having a light chain variable region mutant amino acid sequence of SEQ ID NO:3. In one embodiment, individual host cells in the population harbor an expression vector that is also operably linked to a nucleic acid encoding an antibody heavy chain which comprises a heavy chain variable region wild type amino acid sequence of SEQ ID NO:1. In one embodiment, individual host cells in the population harbor a second expression vector which is operably linked to a nucleic acid encoding an antibody heavy chain which comprises a heavy chain variable region wild type amino acid sequence of SEQ ID NO:1. In one embodiment, the population of host cells express the antibody light chain and heavy chain. In one embodiment, the population of host cells express a fully human IgG class antibody having a light and heavy chain. In one embodiment, the method further comprises: recovering from the population of host cells the expressed antibody light chain. In one embodiment, the method further comprises: recovering from the population of host cells the expressed antibody light and heavy chains. In one embodiment, 90-100% of the expressed and recovered antibody light chains have the correct length, the correct N-terminal amino acid, and have 100% sequence identity to the light chain variable domain of SEQ ID NO:3.

The present disclosure provides a method for preparing a fully human Fab fragment, comprising: culturing a population of the host cell under conditions suitable for expressing the Fab fragment, wherein individual host cells in the population harbor an expression vector operably linked to a nucleic acid encoding an antibody light chain having a light chain variable region mutant amino acid sequence of SEQ ID NO:3. In one embodiment, individual host cells in the population harbor an expression vector that is also operably linked to a nucleic acid encoding the Fab fragment which comprises a heavy chain variable region wild type amino acid sequence of SEQ ID NO:1. In one embodiment, individual host cells in the population harbor a second expression vector which is operably linked to a nucleic acid encoding a Fab fragment heavy chain which comprises a heavy chain variable region wild type amino acid sequence of SEQ ID NO:1. In one embodiment, the population of host cells express the antibody light chain and heavy chain. In one embodiment, the population of host cells express a fully human Fab fragment having a light and heavy chain. In one embodiment, the method further comprises: recovering from the population of host cells the expressed light chain. In one embodiment, the method further comprises: recovering from the population of host cells the expressed light and heavy chains. In one embodiment, 90-100% of the expressed and recovered light chains have the correct length, the correct N-terminal amino acid, and have 100% sequence identity to the light chain variable domain of SEQ ID NO:3.

The present disclosure provides a method for preparing an antigen binding protein (e.g., a single chain antibody, which may be fully human), comprising: culturing a population of the host cell under conditions suitable for expressing the single chain antibody, wherein individual host cells in the population harbor an expression vector operably linked to a nucleic acid encoding an antibody light chain having a light chain variable region mutant amino acid sequence of SEQ ID NO:3. In one embodiment, individual host cells in the population harbor an expression vector that is also operably linked to a nucleic acid encoding the single chain antibody which comprises a heavy chain variable region wild type amino acid sequence of SEQ ID NO:1. In one embodiment, the population of host cells express a fully human single chain antibody having a light chain variable region and a heavy chain variable region. In one embodiment, the method further comprises: recovering from the population of host cells the expressed single chain antibody. In one embodiment, 90-100% of the expressed and recovered single chain antibody have the correct length, the correct N-terminal amino acid, and have 100% sequence identity to the light chain variable domain of SEQ ID NO:3.

Figure 1A:
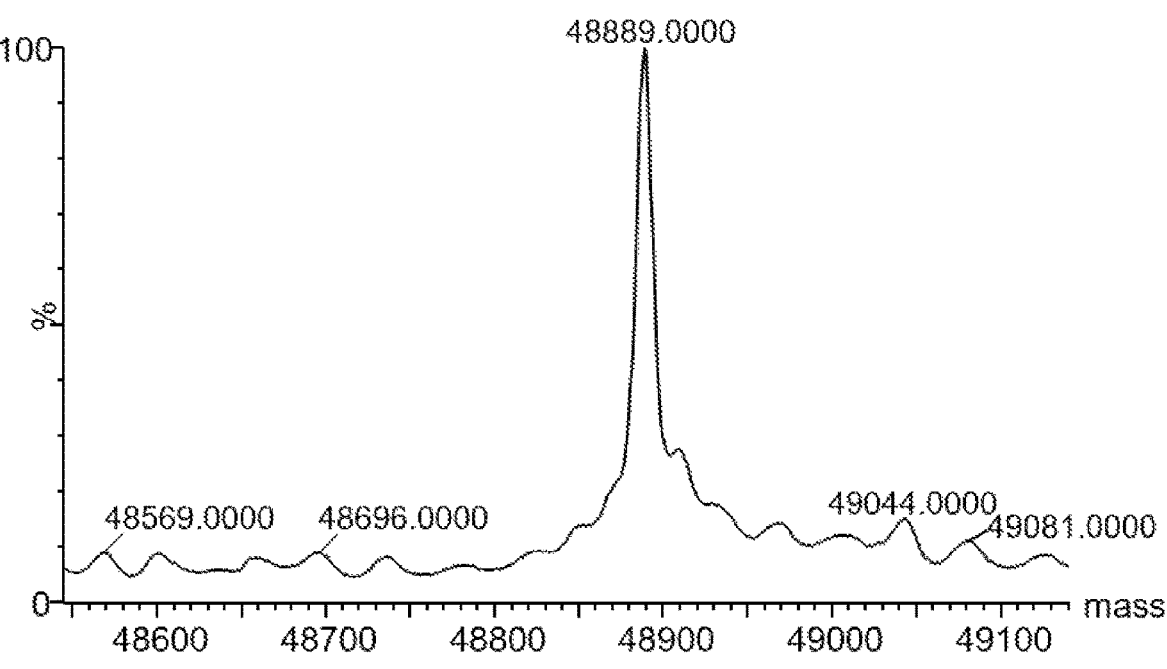
FIG. 1A shows the results of liquid chromatograph-mass spectrophotometry (LC-MS) of the parent wild type CD38 A2 antibody, specifically the reduced, deglycated antibody heavy chain comprising the wild type sequence of SEQ ID NO:1. Peaks are labeled with molecular weights in amu.
Figure 1B:
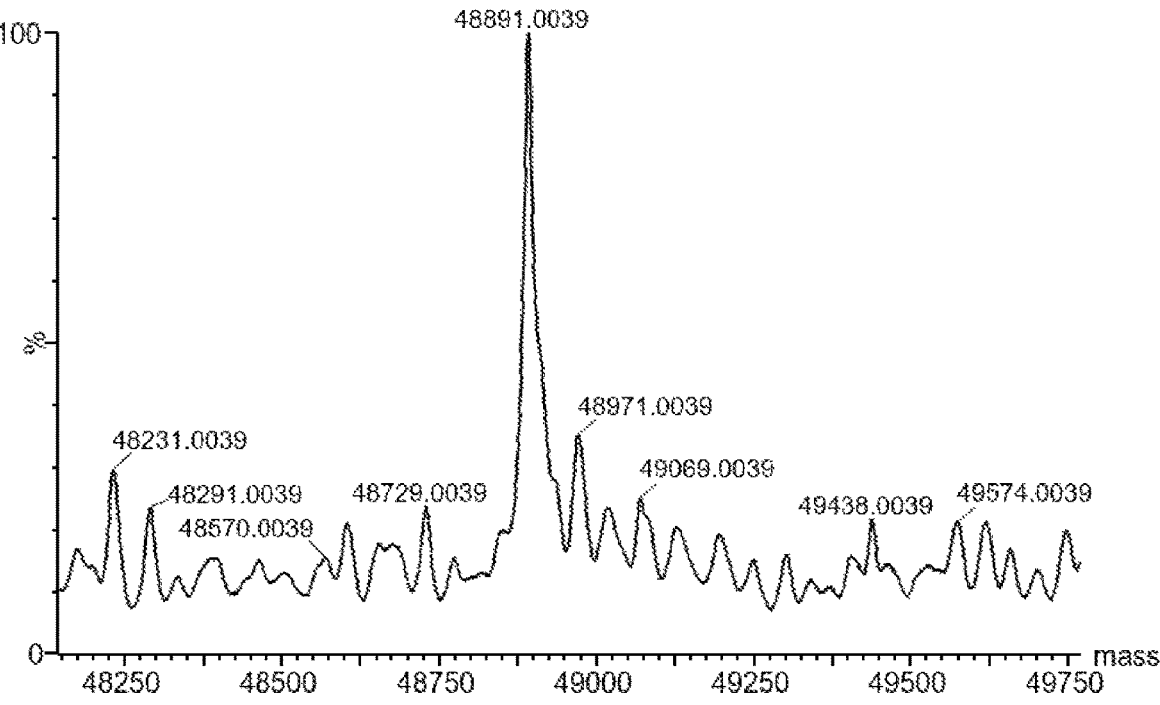
FIG. 1B shows the results of liquid chromatograph-mass spectrophotometry (LC-MS) of the CD38 A2 SV variant antibody, specifically the reduced, deglycated antibody heavy chain comprising the wild type sequence of SEQ ID NO:1. Peaks are labeled with molecular weights in amu.

Unless defined otherwise, technical and scientific terms used herein have meanings that are commonly understood by those of ordinary skill in the art unless defined otherwise. Generally, terminologies pertaining to techniques of cell and tissue culture, molecular biology, immunology, microbiology, genetics, transgenic cell production, protein chemistry and nucleic acid chemistry and hybridization described herein are well known and commonly used in the art. The methods and techniques provided herein are generally performed according to conventional procedures well known in the art and as described in various general and more specific references that are cited and discussed herein unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992). A number of basic texts describe standard antibody production processes, including, Borrebaeck (ed) *Antibody Engineering, 2nd Edition* Freeman and Company, N Y, 1995; McCafferty et al. *Antibody Engineering, A Practical Approach* IRL at Oxford Press, Oxford, England, 1996; and Paul (1995) *Antibody Engineering Protocols* Humana Press, Towata, N.J., 1995; Paul (ed.), *Fundamental Immunology*, Raven Press, N.Y, 1993; Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; *Coding Monoclonal Antibodies: Principles and Practice* (2nd ed.) Academic Press, New York, N.Y., 1986, and Kohler and Milstein *Nature* 256: 495-497, 1975. All of the references cited herein are incorporated herein by reference in their entireties. Enzymatic reactions and enrichment/purification techniques are also well known and are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are well known and commonly used in the art. Standard techniques can be used for chemical syntheses, chemical analyses, pharmaceutical preparation, formulation, and delivery, and treatment of patients.

The headings provided herein are not limitations of the various aspects of the disclosure, which aspects can be understood by reference to the specification as a whole.

Unless otherwise required by context herein, singular terms shall include pluralities and plural terms shall include the singular. Singular forms "a", "an" and "the", and singular use of any word, include plural referents unless expressly and unequivocally limited on one referent.

It is understood the use of the alternative (e.g., "or") herein is taken to mean either one or both or any combination thereof of the alternatives.

The term "and/or" used herein is to be taken mean specific disclosure of each of the specified features or components with or without the other. For example, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

As used herein, terms "comprising", "including", "having" and "containing", and their grammatical variants, as used herein are intended to be non-limiting so that one item or multiple items in a list do not exclude other items that can be substituted or added to the listed items. It is understood that wherever aspects are described herein with the language "comprising," otherwise analogous aspects described in terms of "consisting of" and/or "consisting essentially of" are also provided.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "approximately" can mean within one or more than one standard deviation per the practice in the art. Alternatively, "about" or "approximately" can mean a range of up to 10% (i.e., ±10%) or more depending on the limitations of the measurement system. For example, about 5 mg can include any number between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "approximately" should be assumed to be within an acceptable error range for that particular value or composition.

The terms "peptide", "polypeptide" and "protein" and other related terms used herein are used interchangeably and refer to a polymer of amino acids and are not limited to any particular length. Polypeptides may comprise natural and non-natural amino acids. Polypeptides include recombinant or chemically-synthesized forms. Polypeptides also include precursor molecules that have not yet been subjected to cleavage, for example cleavage by a secretory signal peptide or by non-enzymatic cleavage at certain amino acid residues. Polypeptides include mature molecules that have undergone cleavage. These terms encompass native and artificial proteins, protein fragments and polypeptide analogs (such as muteins, variants, chimeric proteins and fusion proteins) of a protein sequence as well as post-translationally, or otherwise covalently or non-covalently, modified proteins. Polypeptides comprising amino acid sequences of binding proteins that bind CD38 (e.g., anti-CD38 antibodies or antigen-binding portions thereof) prepared using recombinant procedures are described herein.

The terms "nucleic acid", "polynucleotide" and "oligonucleotide" and other related terms used herein are used interchangeably and refer to polymers of nucleotides and are not limited to any particular length. Nucleic acids include recombinant and chemically-synthesized forms. Nucleic acids include DNA molecules (cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. Nucleic acid molecule can be single-stranded or double-stranded. In one embodiment, the nucleic acid molecules of the disclosure comprise a contiguous open reading frame encoding an antibody, or a fragment or scFv, derivative, mutein, or variant thereof. In one embodiment, nucleic acids comprise a one type of polynucleotides or a mixture of two or more different types of polynucleotides. Nucleic acids encoding the antibody light chain, antibody heavy chain, anti-CD38 antibodies or antigen-binding portions thereof, are described herein.

The term "recover" or "recovery" or "recovering", and other related terms, refers to obtaining a protein (e.g., an antibody or an antigen binding portion thereof), from host cell culture medium or from host cell lysate or from the host cell membrane. In one embodiment, the protein is expressed by the host cell as a recombinant protein fused to a secretion signal peptide sequence which mediates secretion of the expressed protein. The secreted protein can be recovered from the host cell medium. In one embodiment, the protein is expressed by the host cell as a recombinant protein that lacks a secretion signal peptide sequence which can be recovered from the host cell lysate. In one embodiment, the protein is expressed by the host cell as a membrane-bound protein which can be recovered using a detergent to release the expressed protein from the host cell membrane. In one embodiment, irrespective of the method used to recover the protein, the protein can be subjected to procedures that remove cellular debris from the recovered protein. For example, the recovered protein can be subjected to chromatography, gel electrophoresis and/or dialysis. In one embodiment, the chromatography comprises any one or any combination or two or more procedures including affinity chromatography, hydroxyapatite chromatography, ion-exchange chromatography, reverse phase chromatography and/or chromatography on silica. In one embodiment, affinity chromatography comprises protein A or G (cell wall components from *Staphylococcus aureus*).

The term "isolated" refers to a protein (e.g., an antibody or an antigen binding portion thereof) or polynucleotide that is substantially free of other cellular material. A protein may be rendered substantially free of naturally associated components (or components associated with a cellular expression system or chemical synthesis methods used to produce the antibody) by isolation, using protein purification techniques well known in the art. The term isolated also refers in some embodiments to protein or polynucleotides that are substantially free of other molecules of the same species, for example other protein or polynucleotides having different amino acid or nucleotide sequences, respectively. The purity of homogeneity of the desired molecule can be assayed using techniques well known in the art, including low resolution methods such as gel electrophoresis and high resolution methods such as HPLC or mass spectrophotometry. In one embodiment, any of the antibody light chain, antibody heavy chain, anti-CD38 antibodies or antigen binding protein thereof can be isolated.

An "antigen binding protein" and related terms used herein refers to a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold. Antigen binding proteins that bind CD38 are described herein.

An antigen binding protein can have, for example, the structure of an immunoglobulin. In one embodiment, an "immunoglobulin" refers to a tetrameric molecule composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two antigen binding sites. In one embodiment, an antigen binding protein can be a synthetic molecule having a structure that differs from a tetrameric immunoglobulin molecule but still binds a target antigen or binds two or more target antigens. For example, a synthetic antigen binding protein can comprise antibody fragments, 1-6 or more polypeptide chains, asymmetrical assemblies of polypeptides, or other synthetic molecules. Antigen binding proteins having immunoglobulin-like properties that bind specifically to CD38 are described herein.

The variable regions of immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4.

One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

The assignment of amino acids to each domain is in accordance with the definitions of Kabat et al. in Sequences of Proteins of Immunological Interest, 5th Ed., US Dept. of Health and Human Services, PHS, NIH, NIH Publication no. 91-3242, 1991. Other numbering systems for the amino acids in immunoglobulin chains include IMGT® (international ImMunoGeneTics information system; Lefranc et al, *Dev. Comp. Immunol.* 29:185-203; 2005) and AHo (Honegger and Pluckthun, *J. Mol. Biol.* 309(3):657-670; 2001); Chothia (Al-Lazikani et al., 1997 Journal of Molecular Biology 273:927-948; Contact (Maccallum et al., 1996 Journal of Molecular Biology 262:732-745, and Aho (Honegger and Pluckthun 2001 Journal of Molecular Biology 309:657-670.

An "antibody" and "antibodies" and related terms used herein refers to an intact immunoglobulin or to an antigen binding portion thereof that binds specifically to an antigen. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

Antibodies include recombinantly produced antibodies and antigen binding portions. Antibodies include non-human, chimeric, humanized and fully human antibodies. Antibodies include monospecific, multispecific (e.g., bispecific, trispecific and higher order specificities). Antibodies include tetrameric antibodies, light chain monomers, heavy chain monomers, light chain dimers, heavy chain dimers. Antibodies include F(ab')$_2$ fragments, Fab' fragments and Fab fragments. Antibodies include single domain antibodies, monovalent antibodies, single chain antibodies, single chain variable fragment (scFv), camelized antibodies, affibodies, disulfide-linked Fvs (sdFv), anti-idiotypic antibodies (anti-Id), minibodies. Antibodies include monoclonal and polyclonal populations. Anti-CD38 antibodies, comprising antibody light and heavy chains are described herein.

An "antigen binding domain," "antigen binding region," or "antigen binding site" and other related terms used herein refer to a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains. Antigen binding domains from anti-CD38 antibodies are described herein.

The terms "specific binding", "specifically binds" or "specifically binding" and other related terms, as used herein in the context of an antibody or antigen binding protein or antibody fragment, refer to non-covalent or covalent preferential binding to an antigen relative to other molecules or moieties (e.g., an antibody specifically binds to a particular antigen relative to other available antigens). In one embodiment, an antibody specifically binds to a target antigen if it binds to the antigen with a dissociation constant $K_D$ of $10^{-5}$ M or less, or $10^{-6}$ M or less, or $10^{-7}$ M or less, or $10^{-8}$ M or less, or $10^{-9}$ M or less, or $10^{-10}$ M or less. Anti-Cd38 antibodies that specifically bind CD38 are described herein.

In one embodiment, a dissociation constant ($K_D$) can be measured using a BIACORE surface plasmon resonance (SPR) assay. Surface plasmon resonance refers to an optical phenomenon that allows for the analysis of real-time interactions by detection of alterations in protein concentrations within a biosensor matrix, for example using the BIACORE system (Biacore Life Sciences division of GE Healthcare, Piscataway, N.J.).

An "epitope" and related terms as used herein refers to a portion of an antigen that is bound by an antigen binding protein (e.g., by an antibody or an antigen binding portion thereof). An epitope can comprise portions of two or more antigens that are bound by an antigen binding protein. An epitope can comprise non-contiguous portions of an antigen or of two or more antigens (e.g., amino acid residues that are not contiguous in an antigen's primary sequence but that, in the context of the antigen's tertiary and quaternary structure, are near enough to each other to be bound by an antigen binding protein). Generally, the variable regions, particularly the CDRs, of an antibody interact with the epitope. Anti-CD38 antibodies, and antigen binding proteins thereof, that bind an epitope of a CD38 polypeptide (antigen) are described herein.

An "antibody fragment", "antibody portion", "antigen-binding fragment of an antibody", or "antigen-binding portion of an antibody" and other related terms used herein refer to a molecule other than an intact antibody that comprises a portion of an intact antibody that binds the antigen to which the intact antibody binds. Examples of antibody fragments include, but are not limited to, Fv, Fab, Fab', Fab'-SH, F(ab')$_2$; Fd; and Fv fragments, as well as dAb; diabodies; linear antibodies; single-chain antibody molecules (e.g. scFv); polypeptides that contain at least a portion of an antibody that is sufficient to confer specific antigen binding to the polypeptide. Antigen binding portions of an antibody may be produced by recombinant DNA techniques or by enzymatic or chemical cleavage of intact antibodies. Antigen binding portions include, inter alia, Fab, Fab', F(ab')2, Fv, domain antibodies (dAbs), and complementarity determining region (CDR) fragments, chimeric antibodies, diabodies, triabodies, tetrabodies, and polypeptides that contain at least a portion of an immunoglobulin that is sufficient to confer antigen binding properties to the antibody fragment. Antigen-binding fragments of anti-CD38 antibodies are described herein.

The terms "Fab", "Fab fragment" and other related terms refers to a monovalent fragment comprising a variable light chain region ($V_L$), constant light chain region ($C_L$), variable heavy chain region ($V_H$), and first constant region ($C_{H1}$). A Fab is capable of binding an antigen. An F(ab')$_2$ fragment is a bivalent fragment comprising two Fab' fragments linked by a disulfide bridge at the hinge region. A F(ab')$_2$ has antigen binding capability. An Fd fragment comprises $V_H$ and $C_{H1}$ regions. An Fv fragment comprises $V_L$ and $V_H$ regions. An Fv can bind an antigen. A dAb fragment has a $V_H$ domain, a $V_L$ domain, or an antigen-binding fragment of a $V_H$ or $V_L$ domain (U.S. Pat. Nos. 6,846,634 and 6,696,245; U.S. published Application Nos. 2002/02512, 2004/0202995, 2004/0038291, 2004/0009507, 2003/0039958;

and Ward et al., Nature 341:544-546, 1989). Fab fragments comprising antigen binding portions from anti-CD38 antibodies are described herein.

A single-chain antibody (scFv) is an antibody in which a $V_L$ and a $V_H$ region are joined via a linker (e.g., a synthetic sequence of amino acid residues) to form a continuous protein chain. Preferably the linker is long enough to allow the protein chain to fold back on itself and form a monovalent antigen binding site (see, e.g., Bird et al., 1988, Science 242:423-26 and Huston et al., 1988, Proc. Natl. Acad. Sci. USA 85:5879-83). Single chain antibodies comprising antigen binding portions from anti-CD38 antibodies are described herein.

Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different. Diabody, tribody and tetrabody constructs can be prepared using antigen binding portions from any of the anti-CD38 antibodies described herein.

The term "human antibody" refers to antibodies that have one or more variable and constant regions derived from human immunoglobulin sequences. In one embodiment, all of the variable and constant domains are derived from human immunoglobulin sequences (e.g., a fully human antibody). These antibodies may be prepared in a variety of ways, examples of which are described below, including through recombinant methodologies or through immunization with an antigen of interest of a mouse that is genetically modified to express antibodies derived from human heavy and/or light chain-encoding genes. Fully human anti-CD38 antibodies and antigen binding proteins thereof are described herein.

A "humanized" antibody refers to an antibody having a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" and related terms used herein refers to an antibody that contains one or more regions from a first antibody and one or more regions from one or more other antibodies. In one embodiment, one or more of the CDRs are derived from a human antibody. In another embodiment, all of the CDRs are derived from a human antibody. In another embodiment, the CDRs from more than one human antibody are mixed and matched in a chimeric antibody. For instance, a chimeric antibody may comprise a CDR1 from the light chain of a first human antibody, a CDR2 and a CDR3 from the light chain of a second human antibody, and the CDRs from the heavy chain from a third antibody. In another example, the CDRs originate from different species such as human and mouse, or human and rabbit, or human and goat. One skilled in the art will appreciate that other combinations are possible.

Further, the framework regions may be derived from one of the same antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind a target antigen). Chimeric antibodies can be prepared from portions of the anti-CD38 antibodies described herein.

As used herein, the term "variant" polypeptides and "variants" of polypeptides refers to a polypeptide comprising an amino acid sequence with one or more amino acid residues inserted into, deleted from and/or substituted into the amino acid sequence relative to a reference polypeptide sequence. Polypeptide variants include fusion proteins. In the same manner, a variant polynucleotide comprises a nucleotide sequence with one or more nucleotides inserted into, deleted from and/or substituted into the nucleotide sequence relative to another polynucleotide sequence. Polynucleotide variants include fusion polynucleotides.

As used herein, the term "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

The term "Fc" or "Fc region" as used herein refers to the portion of an antibody heavy chain constant region ning in or after the hinge region and ending at the C-terminus of the heavy chain. The Fc region comprises at least a portion of the CH and CH3 regions and may, or may not, include a portion of the hinge region. Two polypeptide chains each carrying a half Fc region can dimerize to form a full Fc domain. An Fc domain can bind Fc cell surface receptors and some proteins of the immune complement system. An Fc domain exhibits effector function, including any one or any combination of two or more activities including complement-dependent cytotoxicity (CDC), antibody-dependent cell-mediated cytotoxicity (ADCC), antibody-dependent phagocytosis (ADP), opsonization and/or cell binding. An Fc domain can bind an Fc receptor, including FcγRI (e.g., CD64), FcγRII (e.g, CD32) and/or FcγRIII (e.g., CD16a).

The term "labeled antibody" or related terms as used herein refers to antibodies and their antigen binding portions thereof that are unlabeled or joined to a detectable label or moiety for detection, wherein the detectable label or moiety is radioactive, colorimetric, antigenic, enzymatic, a detectable bead (such as a magnetic or electrodense (e.g., gold) bead), biotin, streptavidin or protein A. A variety of labels can be employed, including, but not limited to, radionuclides, fluorescers, enzymes, enzyme substrates, enzyme cofactors, enzyme inhibitors and ligands (e.g., biotin, haptens). Any of the anti-CD38 antibodies described herein can be unlabeled or can be joined to a detectable label or moiety.

The "percent identity" or "percent homology" and related terms used herein refers to a quantitative measurement of the similarity between two polypeptide or between two polynucleotide sequences. The percent identity between two polypeptide sequences is a function of the number of identical amino acids at aligned positions that are shared between the two polypeptide sequences, taking into account the number of gaps, and the length of each gap, which may need to be introduced to optimize alignment of the two polypeptide sequences. In a similar manner, the percent identity between two polynucleotide sequences is a function of the number of identical nucleotides at aligned positions that are shared between the two polynucleotide sequences, taking into account the number of gaps, and the length of each gap, which may need to be introduced to optimize alignment of the two polynucleotide sequences. A comparison of the sequences and determination of the percent identity between two polypeptide sequences, or between two polynucleotide sequences, may be accomplished using a mathematical algorithm. For example, the "percent identity" or "percent homology" of two polypeptide or two polynucleotide sequences may be determined by comparing the sequences using the GAP computer program (a part of the GCG Wisconsin Package, version 10.3 (Accelrys, San Diego, Calif.)) using its default parameters. Expressions such as "comprises a sequence with at least X % identity to Y" with respect to a test sequence mean that, when aligned to sequence Y as described above, the test sequence comprises residues identical to at least X % of the residues of Y.

In one embodiment, the amino acid sequence of a test antibody may be similar but not identical to any of the amino acid sequences of the light chain and/or heavy chain polypeptides that make up any of the anti-CD38 antibodies, or antigen binding protein thereof, described herein. The similarities between the test antibody and the polypeptides can be at least 95%, or at or at least 96% identical, or at least 97% identical, or at least 98% identical, or at least 99% identical, to any of the light chain and/or heavy chain polypeptides that make up any of the anti-CD38 antibodies, or antigen binding protein thereof, described herein. In one embodiment, similar polypeptides can contain amino acid substitutions within a heavy and/or light chain. In one embodiment, the amino acid substitutions comprise one or more conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference in its entirety. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine.

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen. Antibodies can be produced using recombinant nucleic acid technology as described below.

A "vector" and related terms used herein refers to a nucleic acid molecule (e.g., DNA or RNA) which can be operably linked to foreign genetic material (e.g., nucleic acid transgene). Vectors can be used as a vehicle to introduce foreign genetic material into a cell (e.g., host cell). Vectors can include at least one restriction endonuclease recognition sequence for insertion of the transgene into the vector. Vectors can include at least one gene sequence that confers antibiotic resistance or a selectable characteristic to aid in selection of host cells that harbor a vector-transgene construct. Vectors can be single-stranded or double-stranded nucleic acid molecules. Vectors can be linear or circular nucleic acid molecules. One type of vector is a "plasmid," which refers to a linear or circular double stranded extra-chromosomal DNA molecule which can be linked to a transgene, and is capable of replicating in a host cell, and transcribing and/or translating the transgene. A viral vector typically contains viral RNA or DNA backbone sequences which can be linked to the transgene. The viral backbone sequences can be modified to disable infection but retain insertion of the viral backbone and the co-linked transgene into a host cell genome. Examples of viral vectors include retroviral, lentiviral, adenoviral, adeno-associated, baculoviral, papovaviral, vaccinia viral, herpes simplex viral and Epstein Barr viral vectors. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome.

An "expression vector" is a type of vector that can contain one or more regulatory sequences, such as inducible and/or constitutive promoters and enhancers. Expression vectors can include ribosomal binding sites and/or polyadenylation sites. Regulatory sequences direct transcription, or transcription and translation, of a transgene linked to the expression vector which is transduced into a host cell. The regulatory sequence(s) can control the level, timing and/or location of expression of the transgene. The regulatory sequence can, for example, exert its effects directly on the transgene, or through the action of one or more other molecules (e.g., polypeptides that bind to the regulatory sequence and/or the nucleic acid). Regulatory sequences can be part of a vector. Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-3606. An expression vector can comprise nucleic acids that encode at least a portion of any of the light chain, heavy chain or anti-CD38 antibodies described herein.

A transgene is "operably linked" to a vector when there is linkage between the transgene and the vector to permit functioning or expression of the transgene sequences contained in the vector. In one embodiment, a transgene is "operably linked" to a regulatory sequence when the regulatory sequence affects the expression (e.g., the level, timing, or location of expression) of the transgene.

The terms "transfected" or "transformed" or "transduced" or other related terms used herein refer to a process by which exogenous nucleic acid (e.g., transgene) is transferred or introduced into a host cell. A "transfected" or "transformed" or "transduced" host cell is one which has been transfected, transformed or transduced with exogenous nucleic acid (transgene). The host cell includes the primary subject cell and its progeny. Exogenous nucleic acids encoding at least a portion of any of the light chain, heavy chain or anti-CD38 antibodies described herein can be introduced into a host cell. Expression vectors comprising at least a portion of any of the light chain, heavy chain or anti-CD38 antibodies described herein can be introduced into a host cell, and the host cell can express polypeptides comprising at least a portion of the light chain, heavy chain or anti-CD38 antibody.

The terms "host cell" or "or a population of host cells" or related terms as used herein refer to a cell (or a population thereof) into which foreign (exogenous or transgene) nucleic acids have been introduced. The foreign nucleic acids can include an expression vector operably linked to a transgene, and the host cell can be used to express the nucleic acid and/or polypeptide encoded by the foreign nucleic acid (transgene). A host cell (or a population thereof) can be a cultured cell or can be extracted from a subject. The host cell (or a population thereof) includes the primary subject cell and its progeny without any regard for the number of passages. Progeny cells may or may not harbor identical genetic material compared to the parent cell. Host cells encompass progeny cells. In one embodiment, a host cell describes any cell (including its progeny) that has been modified, transfected, transduced, transformed, and/or manipulated in any way to express an antibody, as disclosed herein. In one example, the host cell (or population thereof) can be introduced with an expression vector operably linked to a nucleic acid encoding the desired antibody, or an antigen binding portion thereof, described herein. Host cells and populations thereof can harbor an expression vector that is stably integrated into the host's genome or can harbor an extrachromosomal expression vector. In one embodiment, host cells and populations thereof can harbor an extrachromosomal vector that is present after several cell divisions or is present transiently and is lost after several cell divisions.

A host cell can be a prokaryote, for example, *E. coli*, or it can be a eukaryote, for example, a single-celled eukaryote (e.g., a yeast or other fungus), a plant cell (e.g., a tobacco or tomato plant cell), an mammalian cell (e.g., a human cell, a monkey cell, a hamster cell, a rat cell, a mouse cell, or an insect cell) or a hybridoma. In one embodiment, a host cell can be introduced with an expression vector operably linked to a nucleic acid encoding a desired antibody thereby generating a transfected/transformed host cell which is cultured under conditions suitable for expression of the antibody by the transfected/transformed host cell, and optionally recovering the antibody from the transfected/transformed host cells (e.g., recovery from host cell lysate) or recovery from the culture medium. In one embodiment, host cells comprise non-human cells including CHO, BHK, NS0, SP2/0, and YB2/0. In one embodiment, host cells comprise human cells including HEK293, HT-1080, Huh-7 and PER.C6. Examples of host cells include the COS-7 line of monkey kidney cells (ATCC CRL 1651) (see Gluzman et al., 1981, Cell 23: 175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B 11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo 205 cells, other transformed primate cell lines, normal diploid cells, cell strains derived from in vitro culture of primary tissue, primary explants, HL-60, U937, HaK or Jurkat cells. In one embodiment, host cells include lymphoid cells such as Y0, NS0 or Sp20. In one embodiment, a host cell is a mammalian host cell, but is not a human host cell. Typically, a host cell is a cultured cell that can be transformed or transfected with a polypeptide-encoding nucleic acid, which can then be expressed in the host cell. The phrase "transgenic host cell" or "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Polypeptides of the present disclosure (e.g., antibodies and antigen binding proteins) can be produced using any methods known in the art. In one example, the polypeptides are produced by recombinant nucleic acid methods by inserting a nucleic acid sequence (e.g., DNA) encoding the polypeptide into a recombinant expression vector which is introduced into a host cell and expressed by the host cell under conditions promoting expression.

General techniques for recombinant nucleic acid manipulations are described for example in Sambrook et al., in *Molecular Cloning: A Laboratory Manual*, Vols. 1-3, Cold Spring Harbor Laboratory Press, 2 ed., 1989, or F. Ausubel et al., in Current Protocols in Molecular Biology (Green Publishing and Wiley-Interscience: New York, 1987) and periodic updates, herein incorporated by reference in their entireties. The nucleic acid (e.g., DNA) encoding the polypeptide is operably linked to an expression vector carrying one or more suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The expression vector can include an origin or replication that confers replication capabilities in the host cell. The expression vector can include a gene that confers selection to facilitate recognition of transgenic host cells (e.g., transformants).

The recombinant DNA can also encode any type of protein tag sequence that may be useful for purifying the protein. Examples of protein tags include but are not limited to a histidine tag, a FLAG tag, a myc tag, an HA tag, or a GST tag. Appropriate cloning and expression vectors for use with bacterial, fungal, yeast, and mammalian cellular hosts can be found in Cloning Vectors: A Laboratory Manual, (Elsevier, N.Y., 1985).

The expression vector construct can be introduced into the host cell using a method appropriate for the host cell. A variety of methods for introducing nucleic acids into host cells are known in the art, including, but not limited to, electroporation; transfection employing calcium chloride, rubidium chloride, calcium phosphate, DEAE-dextran, or other substances; viral transfection; non-viral transfection; microprojectile bombardment; lipofection; and infection (e.g., where the vector is an infectious agent). Suitable host cells include prokaryotes, yeast, mammalian cells, or bacterial cells.

Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow and Summers, (Bio/Technology, 6:47, 1988). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified polypeptides are prepared by culturing suitable host/vector systems to express the recombinant proteins. For many applications, the small size of many of the polypeptides disclosed herein would make expression in *E. coli* as the preferred method for expression. The protein is then purified from culture media or cell extracts. Any of the light chain, heavy chain or anti-CD38 antibodies, or antigen binding protein thereof, can be expressed by transgenic host cells.

Antibodies and antigen binding proteins disclosed herein can also be produced using cell-translation systems. For such purposes the nucleic acids encoding the polypeptide must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system.

Nucleic acids encoding any of the various polypeptides disclosed herein may be synthesized chemically. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., Proc. Natl. Acad. Sci. USA. 2003 100(2):438-42; Sinclair et al. Protein Expr. Purif. 2002 (1):96-105; Connell N D. Curr. Opin. Biotechnol. 2001 12(5):446-9; Makrides et al. Microbiol. Rev. 1996 60(3):512-38; and Sharp et al. Yeast. 1991 7(7):657-78.

Antibodies and antigen binding proteins described herein can also be produced by chemical synthesis (e.g., by the methods described in Solid Phase Peptide Synthesis, 2nd ed., 1984, The Pierce Chemical Co., Rockford, Ill.). Modifications to the protein can also be produced by chemical synthesis.

Antibodies and antigen binding proteins described herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, polypeptides may be exchanged into different buffers and/or concentrated by any of a variety of methods known to the art, including, but not limited to, filtration and dialysis.

The purified antibodies and antigen binding proteins described herein are preferably at least 65% pure, at least 75% pure, at least 85% pure, more preferably at least 95% pure, and most preferably at least 98% pure. Regardless of the exact numerical value of the purity, the polypeptide is sufficiently pure for use as a pharmaceutical product. Any of the light chain, heavy chain or anti-CD38 antibodies, or antigen binding protein thereof, described herein can be expressed by transgenic host cells and then purified to about 65-98% purity or high level of purity using any art-known method.

In certain embodiments, the antibodies and antigen binding proteins herein can further comprise post-translational modifications. Exemplary post-translational protein modifications include phosphorylation, acetylation, methylation, ADP-ribosylation, ubiquitination, glycosylation, carbonylation, sumoylation, biotinylation or addition of a polypeptide side chain or of a hydrophobic group. As a result, the modified polypeptides may contain non-amino acid elements, such as lipids, poly- or mono-saccharide, and phosphates. A preferred form of glycosylation is sialylation, which conjugates one or more sialic acid moieties to the polypeptide. Sialic acid moieties improve solubility and serum half-life while also reducing the possible immunogenicity of the protein. See Raju et al. Biochemistry. 2001 31; 40(30):8868-76.

In one embodiment, the antibodies and antigen binding proteins described herein can be modified to become soluble polypeptides which comprises linking the Antibodies and antigen binding proteins to non-proteinaceous polymers. In one embodiment, the non-proteinaceous polymer comprises polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: X—O (CH$_2$CH$_2$O)$_n$—CH$_2$CH$_2$OH (1), where n is 20 to 2300 and X is H or a terminal modification, e.g., a C$_{1-4}$ alkyl. In one embodiment, the PEG terminates on one end with hydroxy or methoxy, i.e., X is H or CH$_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini et al., Bioconjugate Chem. 6 (1995) 62-69).

The serum clearance rate of PEG-modified polypeptide may be modulated (e.g., increased or decreased) by about 10%, 20%, 30%, 40%, 50%, 60%, 70%, 80%, or even 90%, relative to the clearance rate of the unmodified antibodies and antigen binding proteins binding polypeptides. The PEG-modified antibodies and antigen binding proteins may have a half-life (t$_{1/2}$) which is enhanced relative to the half-life of the unmodified polypeptide. The half-life of PEG-modified polypeptide may be enhanced by at least 10%, 20%, 30%, 40%, 50%, 60%, 70%, 80%, 90%, 100%, 125%, 150%, 175%, 200%, 250%, 300%, 400% or 500%, or even by 1000% relative to the half-life of the unmodified antibodies and antigen binding proteins. In some embodiments, the protein half-life is determined in vitro, such as in a buffered saline solution or in serum. In other embodiments, the protein half-life is an in vivo half-life, such as the half-life of the protein in the serum or other bodily fluid of an animal.

The present disclosure provides therapeutic compositions comprising any of the light chain, heavy chain or anti-CD38 antibodies, or antigen binding protein thereof, described herein in an admixture with a pharmaceutically-acceptable excipient. An excipient encompasses carriers, stabilizers and excipients. Excipients of pharmaceutically acceptable excipients includes for example inert diluents or fillers (e.g., sucrose and sorbitol), lubricating agents, glidants, and anti-adhesives (e.g., magnesium stearate, zinc stearate, stearic acid, silicas, hydrogenated vegetable oils, or talc). Additional examples include buffering agents, stabilizing agents, preservatives, non-ionic detergents, anti-oxidants and iso-tonifiers.

Therapeutic compositions and methods for preparing them are well known in the art and are found, for example, in "Remington: The Science and Practice of Pharmacy" (20th ed., ed. A. R. Gennaro A R., 2000, Lippincott Williams & Wilkins, Philadelphia, Pa.). Therapeutic compositions can be formulated for parenteral administration may, and can for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the antibody (or antigen binding protein thereof) described herein. Nanoparticulate formulations (e.g., biodegradable nanoparticles, solid lipid nanoparticles, liposomes) may be used to control the biodistribution of the antibody (or antigen binding protein thereof). Other potentially useful parenteral delivery systems include ethylene-vinyl acetate copolymer particles, osmotic pumps, implantable infusion systems, and liposomes. The concentration of the antibody (or antigen binding protein thereof) in the formulation varies depending upon a number of factors, including the dosage of the drug to be administered, and the route of administration.

Any of the anti-CD38 antibodies (or antigen binding portions thereof) may be administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like. In one example, the antibody (or antigen binding portions thereof) is formulated in the presence of sodium acetate to increase thermal stability.

Any of the anti-CD38 antibodies (or antigen binding portions thereof) may be formulated for oral use include tablets containing the active ingredient(s) in a mixture with non-toxic pharmaceutically acceptable excipients. Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The term "subject" as used herein refers to human and non-human animals, including vertebrates, mammals and non-mammals. In one embodiment, the subject can be human, non-human primates, simian, ape, murine (e.g., mice and rats), bovine, porcine, equine, canine, feline, caprine, lupine, ranine or piscine.

The term "administering", "administered" and grammatical variants refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods. Any of the anti-CD38 antibodies described herein (or antigen binding protein thereof) can be administered to a subject using art-known methods and delivery routes.

The terms "effective amount", "therapeutically effective amount" or "effective dose" or related terms may be used interchangeably and refer to an amount of antibody or an antigen binding protein (e.g., any of the anti-CD38 antibodies described herein or antigen binding protein thereof) that when administered to a subject, is sufficient to effect a measurable improvement or prevention of a disease or disorder associated with tumor or cancer antigen expression. Therapeutically effective amounts of antibodies provided herein, when used alone or in combination, will vary depending upon the relative activity of the antibodies and combinations (e.g., in inhibiting cell growth) and depending upon the subject and disease condition being treated, the weight and age and sex of the subject, the severity of the disease condition in the subject, the manner of administration and the like, which can readily be determined by one of ordinary skill in the art.

In one embodiment, a therapeutically effective amount will depend on certain aspects of the subject to be treated and the disorder to be treated and may be ascertained by one skilled in the art using known techniques. In general, the polypeptide is administered at about 0.01 g/kg to about 50 mg/kg per day, preferably 0.01 mg/kg to about 30 mg/kg per day, most preferably 0.1 mg/kg to about 20 mg/kg per day. The polypeptide may be administered daily (e.g., once, twice, three times, or four times daily) or preferably less frequently (e.g., weekly, every two weeks, every three weeks, monthly, or quarterly). In addition, as is known in the art, adjustments for age as well as the body weight, general health, sex, diet, time of administration, drug interaction, and the severity of the disease may be necessary.

The present disclosure provides methods for treating a subject having a disease associated with expression of CD38. The disease comprises cancer or tumor cells expressing the tumor-associated antigens. In one embodiment, the cancer or tumor includes cancer of the prostate, breast, ovary, head and neck, bladder, skin, colorectal, anus, rectum, pancreas, lung (including non-small cell lung and small cell lung cancers), leiomyoma, brain, glioma, glioblastoma, esophagus, liver, kidney, stomach, colon, cervix, uterus, endometrium, vulva, larynx, vagina, bone, nasal cavity, paranasal sinus, nasopharynx, oral cavity, oropharynx, larynx, hypolarynx, salivary glands, ureter, urethra, penis and testis.

In one embodiment, the cancer comprises hematological cancers, including leukemias, lymphomas, myelomas and B cell lymphomas. Hematologic cancers include multiple myeloma (MM), non-Hodgkin's lymphoma (NHL) including Burkitt's lymphoma (BL), B chronic lymphocytic leukemia (B-CLL), systemic lupus erythematosus (SLE), B and T acute lymphocytic leukemia (ALL), acute myeloid leukemia (AML), chronic lymphocytic leukemia (CLL), diffuse large B cell lymphoma, chronic myelogenous leukemia (CML), hairy cell leukemia (HCL), follicular lymphoma, Waldenstrom's Macroglobulinemia, mantle cell lymphoma, Hodgkin's Lymphoma (HL), plasma cell myeloma, precursor B cell lymphoblastic leukemia/lymphoma, plasmacytoma, giant cell myeloma, plasma cell myeloma, heavy-chain myeloma, light chain or Bence-Jones myeloma, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome. Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, and monoclonal gammopathy of underdetermined significance.

An anti-CD38 antibody is disclosed in U.S. patent application Ser. No. 15/094,384 filed 8 Apr. 2016 (the disclosure of which is incorporated by reference herein in its entirety). This antibody, referred to herein as the "parent" and/or "wild type" antibody, comprises a parent wild type heavy chain having a heavy variable region comprising the amino acid sequence of SEQ ID NO:1, and a parent wild type light chain having a light variable region comprising the amino acid sequence of SEQ ID NO:2.

The present disclosure provides a variant antibody comprising a parent wild type heavy chain having a heavy variable region comprising the amino acid sequence of SEQ ID NO:1 and light chain having a light chain variable region comprising the mutant amino acid sequence of SEQ ID NO:3. In some embodiments, the present disclosure provides methods of preparing the variant sequence light chain or an antigen binding protein comprising the variant sequence light chain, wherein the mutant amino acid sequence of the light chain reduces or eliminates the generation of a heterogenous population of light chains which contain a mixture of the desirable and undesirable light chains. In contrast, making a preparation of the parent wild type light chain produces a population of antibody light chains having a high level of heterogeneity.

Recombinant antibody heavy and light chains are often designed to include a secretory signal peptide at their N-terminal end to enable expression of precursor antibody chains in the host cell cytoplasm and translocation across the host cell membrane. The translocating precursor antibody chain undergoes site-specific cleavage at the secretory signal peptide by signal peptide peptidase enzymes expressed by the host cell, resulting in a mature antibody chain. It is desirable to generate a homogeneous population of a mature antibody chain from a precursor antibody chain that has been cleaved at a specific site in the secretory signal peptide to yield a population of mature antibody chains having the same length and sequence and with the same N- and C-terminal ends. However, production of recombinant antibody chains often generates a heterogeneous population having different chain lengths and sequences, and different N- and/or C-terminal ends. One source of heterogeneity arises from cleavage of the secretory signal peptide or the N-terminal region of the antibody chain at variable sites, which gives rise to chain truncation and elongation. Cleavage heterogeneity is also known to arise from non-enzymatic degradation of peptide bonds in and near the secretory signal peptide, for example at certain amino acids such as aspartic acid, glycine, serine, threonine, cysteine, methionine or asparagine. Regardless of the mechanism that leads to cleavage heterogeneity, imprecise cleavage gives rise to antibody chain population heterogeneity. Cleavage heterogeneity can reduce antibody binding to its target antigen. In some cases, cleavage heterogeneity alters the charge of an antibody chain leading to undesirable changes in antibody pI (isoelectric point) values, thereby leading to charge heterogeneity in a population of expressed antibody chains. Overall, cleavage heterogeneity can reduce antibody efficacy, reduce storage life, and makes it difficult to consistently produce a homogeneous product, making an antibody chain less desirable or unsuitable for bioproduction.

The present disclosure provides a variant antibody light chain having a mutated amino acid sequence that is designed to reduce cleavage heterogeneity that occurs during host cell expression, thereby reducing light chain population heterogeneity. The antibody light chain comprises an amino acid sequence that is mutated near its N-terminal end, which abuts a secretory signal peptide, to reduce cleavage heterogeneity. Without wishing to be bound by theory, it is postulated that the amino acid mutation in the antibody light chain described herein reduces cleavage heterogeneity due to enzymatic and/or non-enzymatic cleavage events.

A heterogeneous population of antibody light chains comprises a mixture of desirable and undesirable light chains. The desirable light chains have the correct length, the correct N- and C-terminal amino acid residues, and comprise a light chain variable region having the amino acid sequence that is 100% identical to SEQ ID NO:3. In some embodiments, the desirable chain is the plurality or majority species in the population of chains. The undesirable light chains have an incorrect length (e.g., longer or shorter), incorrect N- and/or C-terminal amino acid residue, and/or comprise a light chain variable region having an amino acid sequence that is not 100% identical to SEQ ID NO:3.

In the following discussion, increases, decreases, and reductions are expressed relative to SEQ ID NO:2. In some embodiments, the light chain sequence mutation reduces the generation of a heterogenous population of light chains by increasing the percentage of desirable light chains and decreasing or even eliminating the percentage of undesirable light chains.

In some embodiments, the light chain sequence mutation reduces the percentage of undesirable light chains in a preparation of the light chain (e.g., in a population of light chains) by about 10-30%, or about 30-50%, or about 50-70%, or about 70-90%, or about 90-95%, or about 95-99% or higher levels.

In some embodiments, the light chain sequence mutation increases the percentage of desirable light chains in a preparation of the light chain (e.g., in a population of light chains) by about 10-30%, or about 30-50%, or about 50-70%, or about 70-90%, or about 90-95%, or about 95-99% or higher levels.

Figure 2A:
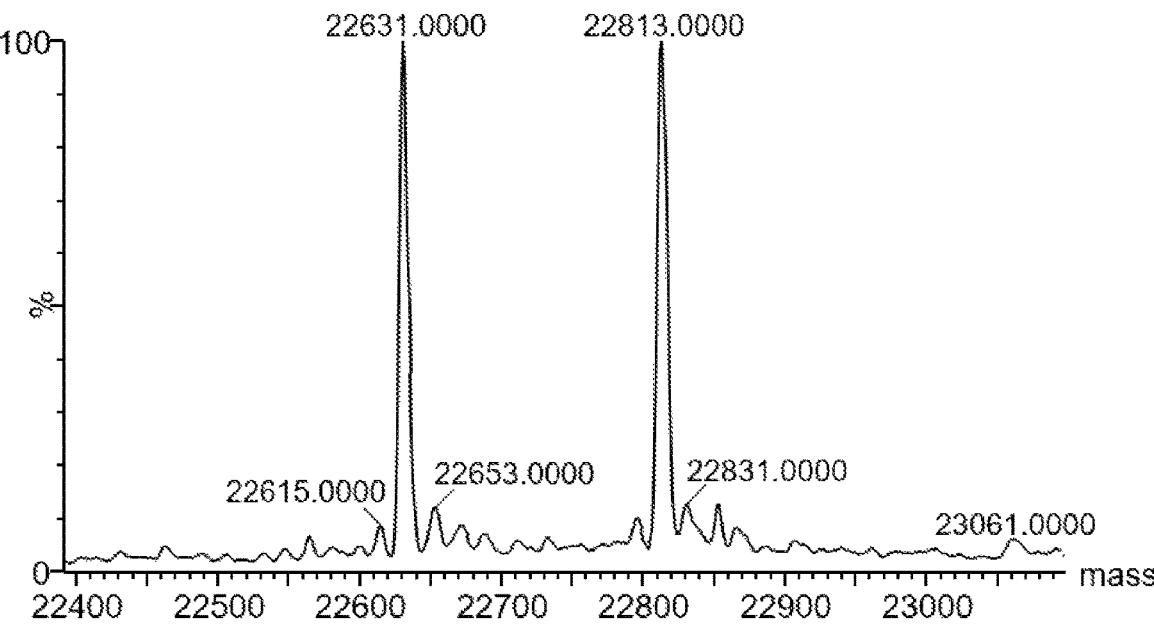
FIG. 2A shows the results of liquid chromatograph-mass spectrophotometry (LC-MS) of the parent wild type CD38 A2 antibody, specifically the antibody light chain comprising the wild type sequence of SEQ ID NO:2. Peaks are labeled with molecular weights in amu.
Figure 2B:
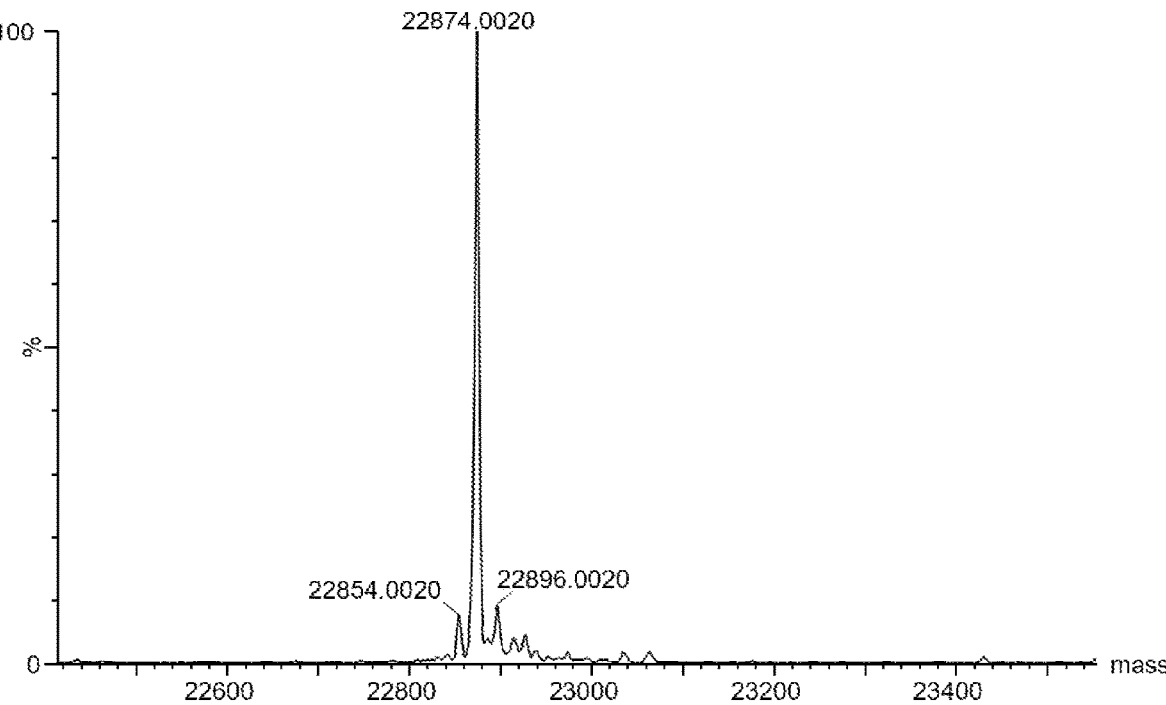
FIG. 2B shows the results of liquid chromatograph-mass spectrophotometry (LC-MS) of the variant CD38 A2 SV variant antibody, specifically the antibody light chain comprising the variant sequence of SEQ ID NO:3. Peaks are labeled with molecular weights in amu.

In one embodiment, the light chain sequence mutation comprises two point mutations near the N-terminal end, specifically alanine at position 2 is replaced with serine, and glycine at position 3 is replaced with valine (see positions 2 and 3 of SEQ ID NO:3). The light chain sequence mutation increases the percentage of desirable light chains so that a preparation of the mutant light chains contains about 98-100% desirable light chain having the correct length, the correct N-terminal amino acid, and have 100% sequence (FIGS. 2A and B).

In one embodiment, the light chain sequence mutation comprises the amino acid sequence of SEQ ID NO:2 having two point mutations near the N-terminal end, specifically alanine at position 2 is replaced with serine, and glycine at position 3 is replaced with alanine. In one embodiment, the N-terminal end of the mutant light chain contains the amino acid sequence QSALT (SEQ ID NO: 6). The light chain sequence mutation increases the percentage of desirable light chains so that a preparation of the mutant light chains contains about 98-100% desirable light chain having the correct length, the correct N-terminal amino acid, and have 100% sequence (Table 2).

The light chain mutant sequence described herein can provide reduced cleavage heterogeneity and improves production and yield of antibody light chains. The type and/or sequence of the secretory signal peptide that is operably linked to the antibody light chain is not important.

In contrast, the parent wild type light chain (SEQ ID NO:2) gives rise to a heterogeneous mixture of undesirable and desirable light chains. A preparation of the parent wild type light chain can generate a high percentage of truncated light chains where as much as 35-65% of the light chains are the undesirable truncated light chains (see Table 2 and FIGS. 2A and B). For example, a preparation of the parent wild type light chain can contain about 10-30%, or about 30-50%, or about 50-70%, or about 70-90%, or about 90-95%, or about 95-99% or higher levels of the undesirable truncated light chain form.

The present disclosure provides a host cell that expresses a precursor polypeptide comprising the amino acid sequence of a secretory signal peptide which is operably linked to the mutant amino acid sequence of the antibody light chain having a light chain variable region comprising the amino acid sequence of SEQ ID NO:3. In one embodiment, the secretory signal peptide directs movement of the precursor polypeptide to the endoplasmic reticulum, secretory vesicles and/or extracellular space. In one embodiment, the secretory signal peptide mediates secretion of the precursor polypeptide from the host cell. In one embodiment, the secretory signal peptide serves as a substrate for enzymatic cleavage at a specific site (e.g., desired cleavage site) in the secretory signal peptide to yield a mature polypeptide which is shorter than the precursor polypeptide. In one embodiment, the cleavage event yields an antibody light chain having the correct length and carrying a new N-terminal end and comprises an amino acid sequence that is 100% identical to the amino acid sequence of SEQ ID NO:3. The mutated antibody light chain can assemble with a heavy chain to generate an immunoglobulin that binds its target antigen CD38.

The present disclosure provides the mutated light chain assemble with the heavy chain to form an antigen binding protein that binds specifically to CD38 antigen, and nucleic acids that encode the antigen binding proteins, vectors comprising the nucleic acids, host cells harboring the vectors, and method of use thereof.

Host cell expression of antibody heavy and light chains can be used to make a preparation of a population of an antibody including the variant antibody and parent wild type antibody.

The host cells can express a parent wild type heavy chain having a wild type sequence. The preparation of the parent wild type heavy chain may contain about 85-99% or higher levels of the desirable heavy chain sequence (e.g., low level of heavy chain heterogeneity). The host cells can express a parent wild type sequence light chain having a wild type sequence. The preparation of the parent wild type light chain may contain about 40-55% or higher levels of undesirable light chain sequence (e.g., high level of light chain heterogeneity).

The host cells can express a parent wild type heavy chain having a wild type sequence. The preparation of the parent wild type heavy chain may contain about 85-99% or higher levels of the desirable heavy chain sequence (e.g., low level of heavy chain heterogeneity). The host cells can express a variant sequence light chain having a mutant sequence. The preparation of the variant sequence light chain may contain about 85-99% or higher levels of desirable light chain sequence which is a reduced levels of light chain heterogeneity compared to a preparation of the parent wild type light chain.

The present disclosure provides a fully human antibody of an IgG class that binds to a CD38 polypeptide. In one embodiment, the anti-CD38 antibody comprises a heavy chain variable region having at least 95% sequence identity, or at least 96% sequence identity, or at least 97% sequence identity, or at least 98% sequence identity, or at least 99% sequence identity to the amino acid sequence of SEQ ID NO:1; and the anti-CD38 antibody comprises a light chain variable region having 95% sequence identity, or at least 96% sequence identity, or at least 97% sequence identity, or at least 98% sequence identity, or at least 99% sequence identity to the amino acid sequence of SEQ ID NO:3. In one embodiment, the anti-CD38 antibody comprises an IgG1, IgG2, IgG3 or IgG4 class antibody. In one embodiment, the anti-CD38 antibody comprises an IgG1 or IgG4 class antibody.

In one embodiment, the anti-CD38 antibody, or fragment thereof, comprises an antigen binding portion that binds an epitope of a CD38 target antigen with a binding affinity ($K_D$) of $10^{-6}$ M or less, $10^{-7}$ M or less, $10^{-8}$ M or less, $10^{-9}$ M or less, or $10^{-10}$ M or less (see Table 3). In one embodiment, the CD38 antigen comprises a cell surface CD38 antigen or a soluble CD38 antigen. In one embodiment, the CD38 antigen comprises an extracellular portion of a cell surface CD38 antigen. In one embodiment, the CD38 antigen comprises a human or non-human CD38 antigen. In one embodiment, the CD38 antigen is expressed by a human or non-human cell. In one embodiment, the anti-CD38 antibody binds a human CD38 expressed by a human B cell or expressed by a human multiple myeloma cell. In one embodiment, binding between the anti-CD38 antibody, or fragment thereof, can be detected and measured using surface plasmon resonance, flow cytometry and/or ELISA.

The present disclosure provides an anti-CD38 antibody which binds an epitope of CD38 from a human, or can bind (e.g., cross-reactivity) with an epitope of CD38 (e.g., homologous antigen) from any one or any combination of non-human animals such as mouse, rat, goat, rabbit, hamster and/or monkey (e.g., cynomolgus). In one embodiment, the anti-CD38 antibody binds mouse CD38 with a binding affinity $K_D$ of $10^{-5}$ M or less, or $10^{-6}$ M or less, or $10^{-7}$ M or less, or $10^{-8}$ M or less, or $10^{-9}$ M or less, or $10^{-10}$ M or less. In one embodiment, the anti-CD38 antibody binds cynomolgus CD38 with a binding affinity $K_D$ of $10^{-5}$ M or less, or $10^{-6}$ M or less, or $10^{-7}$ M or less, or $10^{-8}$ M or less, or $10^{-9}$ M or less, or $10^{-10}$ M or less.

The present disclosure provides a fully human antibody that binds CD38 wherein the antibody comprises both heavy and light chains, wherein the heavy/light chain variable region amino acid sequences have at least 95% sequence identity, or at least 96% sequence identity, or at least 97% sequence identity, or at least 98% sequence identity, or at least 99% sequence identity to the amino acid sequence set SEQ ID NOS:1 and 3.

The present disclosure provides a Fab fully human antibody fragment, comprising a heavy variable region from a heavy chain and a variable region from a light chain. The sequence of the variable region from the heavy chain is at least 95% identical, or at least 96% identical, or at least 97% identical, or at least 98% identical, or at least 99% identical to the amino acid sequence of SEQ ID NO:1. The sequence of the variable region from the light chain is at least 95% identical, or at least 96% identical, or at least 97% identical, or at least 98% identical, or at least 99% identical to the amino acid sequence of SEQ ID NO:3.

The present disclosure provides a Fab fully human antibody fragment, comprising a heavy chain variable region and a light chain variable region, wherein the heavy/light chain variable region amino acid sequences are at least 95% identical, or at least 96% identical, or at least 97% identical, or at least 98% identical, or at least 99% identical to any of the following amino acid sequence sets: SEQ ID NOS:1 and 3.

The present disclosure provides a single chain fully human antibody comprising a polypeptide chain having a variable region from a fully human heavy chain and a variable region from a fully human light chain, and optionally a linker joining the variable heavy and variable light chain regions, wherein the variable heavy region comprises at least 95% sequence identity, or at least 96% sequence identity, or at least 97% sequence identity, or at least 98% sequence identity, or at least 99% sequence identity to the amino acid sequence of SEQ ID NO:1. The variable light region comprises at least 95% sequence identity, or at least 96% sequence identity, or at least 97% sequence identity, or at least 98% sequence identity, or at least 99% sequence identity to the amino acid sequence of SEQ ID NO:3.

The present disclosure provides a single chain fully human antibody comprising a polypeptide chain having heavy chain variable region and a light chain variable region, wherein the heavy/light chain variable region amino acid sequence sets are at least 95% identical, or at least 96% identical, or at least 97% identical, or at least 98% identical, or at least 99% identical to any of the following amino acid sequence sets: SEQ ID NOS:1 and 3.

The present disclosure provides therapeutic compositions comprising any of the anti-CD38 antibodies described herein, or antigen binding protein thereof, in an admixture with a pharmaceutically-acceptable excipient. An excipient encompasses carriers and stabilizers. In one embodiment, the therapeutic compositions comprise an anti-CD38 antibody, or antigen binding fragment thereof, comprising a heavy chain variable region and a light chain variable region, wherein the heavy/light chain variable region amino acid sequences are at least 95% identical, or at least 96% identical, or at least 97% identical, or at least 98% identical, or at least 99% identical to any of the following amino acid sequence sets: SEQ ID NOS:1 and 3.

The present disclosure provides methods for treating a subject having a disease associated with CD38 expression, the method comprising: administering to the subject an effective amount of a therapeutic composition comprising an anti-CD38 antibody or antigen binding fragment thereof, which is selected from a group consisting of any of the fully human anti-CD38 antibodies described herein, any of the Fab fully human anti-CD38 antibodies described herein, and any of the single chain human anti-CD38 antibodies described herein. In one embodiment, the disease associated with CD38 expression is a hematological cancer, including leukemia, lymphoma, myeloma or B cell lymphoma. In one embodiment, the hematologic cancers include multiple myeloma (MM), non-Hodgkin's lymphoma (NHL) including Burkitt's lymphoma (BL), B chronic lymphocytic leukemia (B-CLL), systemic lupus erythematosus (SLE), B and T acute lymphocytic leukemia (ALL), acute myeloid leukemia (AML), chronic lymphocytic leukemia (CLL), diffuse large B cell lymphoma, chronic myelogenous leukemia (CML), hairy cell leukemia (HCL), follicular lymphoma, Waldenstrom's Macroglobulinemia, mantle cell lymphoma, Hodgkin's Lymphoma (HL), plasma cell myeloma, precursor B cell lymphoblastic leukemia/lymphoma, plasmacytoma, giant cell myeloma, plasma cell myeloma, heavy-chain myeloma, light chain or Bence-Jones myeloma, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, and monoclonal gammopathy of undetermined significance.

LIST OF SEQUENCES

TABLE 1

| Heavy chain variable region: | Light chain variable region: |
|---|---|
| CD38-A2 wild type SEQ ID NO: 1 QVQLVESGGGLVKPGGSLRLSCAASGFTF SDDYMSWIRQAPGKGLEWVASVSNGRPTT YYADSVRGRFTISRDNAKNSLYLQMNSLR AEDTAVYYCAREDWGGEFTDWGRGTLVTV SS | CD38-A2 wild type SEQ ID NO: 2 QAGLTQPPSASGTSGQR VTISCSGSSSNIGINFV YWYQHLPGTAPKLLIYK NNQRPSGVPDRFSGSKS GNSASLAISGLRSEDEA DYYCAAWDDSLSGYVFG SGTKVTVL |
| CD38-A2 SV mutant SEQ ID NO: 1 QVQLVESGGGLVKPGGSLRLSCAASGFTF SDDYMSWIRQAPGKGLEWVASVSNGRPTT YYADSVRGRFTISRDNAKNSLYLQMNSLR AEDTAVYYCAREDWGGEFTDWGRGTLVTV SS | CD38-A2 SV mutant SEQ ID NO: 3 QSVLTQPPSASGTSGQR VTISCSGSSSNIGINFV YWYQHLPGTAPKLLIYK NNQRPSGVPDRFSGSKS GNSASLAISGLRSEDEA DYYCAAWDDSLSGYVFG SGTKVTVL |

EXAMPLES

The following examples are meant to be illustrative and can be used to further understand embodiments of the present disclosure and should not be construed as limiting the scope of the present teachings in any way.

Example 1: Synthesis of Mutant Light Chain for CD38-A2 Antibody

A synthesized codon-optimized DNA fragment was obtained which encoded the light chain for CD38-A2 SV mutant antibody. The fragment contained two point mutations near the encoded N-terminal end, specifically alanine at position 2 was replaced with serine, and glycine at position 3 was replaced with valine. The fragment encoding the light chain was inserted in-frame into a Lonza pXC-17.4 vector and a different fragment encoding the wild type CD38-A2 heavy chain was inserted in-frame into a Lonza pXC-18.4 vector (Lonza GS System from Lonza, Basel, Switzerland) using standard restriction enzyme digestion and ligation. The pXC-17.4 and pXC18.4 vectors were fused into a single vector using standard enzyme digestion and ligation, and the resulting fused vector was introduced into *E. coli* host cells.

Example 2: Liquid Chromatography Mass Spectrophotometry Analysis of Mutant Light Chains from an Anti-CD38 Antibody Reduced LC-MS analysis was performed to compare CD38-A2 wild type (WT) and CD38-A2 SV variant antibodies. Briefly, 16 μL of antibody sample (20 μg) was mixed with 4 μL 5× Rapid PNGase buffer (Catalog: P0710S; NEB) and incubated at 80° C. for 5 min to reduce disulfide bonds and denature the protein. 0.5 μL of Rapid PNGase F (Catalog: P0710S; NEB) was then added to release N-glycans at 50° C. for 15 min. Five micrograms of sample was injected onto Waters LC-ESI-MS system.

An ACQUITY UPLC® System equipped with 2.1×150 mm BEH 300 Å 1.7 μm C4 Column was used for the separation of reduced antibody chains and the column temperature was 80° C. Antibody was eluted from the column with a 12 min gradient (25-40% Acetonitrile/0.1% formic acid, 0.4 mL/min flow rate).

A Waters Xevo G2 TOF MS System was run in positive ion, sensitivity mode with detection in the range of 400-4000 m/z. Source parameters were as follows: capillary voltage, 3.10 kV; sampling cone voltage, 40.0 V; Extraction Cone voltage, 3.0 V; source temperature, 125° C.; desolvation temperature, 350° C.; cone gas flow: 10 L/hr; desolvation gas flow, 500 L/hr. The protein peak was deconvoluted by the MassLynx MaxEnt1 function according to the following parameters: output resolution, 1.0 Da/channel; output mass range, 20,000-70,000 Da for reduced antibody; uniform Gaussian width at half height, 0.75 Da; minimum intensity ratios, 33% for left and right; maximum number of iterations, 12.

The molecular weights of CD38A2 WT and SV variant were measured by LC-ESI-MS, which confirmed the protein ID. Both WT and SV heavy chain molecule weights matched well with theoretical mass. Meanwhile, the truncation of 2 amino acids from N-terminal Light Chain were found in up to ~50% of total wild type light chains. The LC of SV mutant did not show any detectable truncation.

Reducing CE-SDS was performed on the test samples using an Agilent Bioanalyzer 2100 followed manufacture instructions. Two light chain populations with a ratio of about 1:1 were detected on a reduced CE-SDS for CD38-A2 wild type. The CD38-A2 SV mutant only showed one light chain on reduced CE-SDS. The result is consistent with the findings from LC-MS analysis that the wild type undergoes light chain truncation.

Mass spectrometry and reduced CE-SDS results show that approximately 50% of the population of CD38-A2 wild type light chains are truncated molecules.

In conclusion, according to LC-MS and CE-SDS analysis, N-terminal light chain truncation occurred in CD38-A2 wild type, but was undetectable for the CD38-A2 SV variant. The results are summarized in Table 2 and FIGS. 1A and B and 2A and B. Results are also shown for a CD38 A2-SA variant in which the second and third amino acids of the light chain were serine and alanine, respectively.

TABLE 2

| Light Chain N-terminal sequence | Reduced and Deglycated LC-MS | | Reduced CE_SDS | |
|---|---|---|---|---|
| | Full | LC Truncated (−2AA) | Full | LC Truncated (−2AA) |
| Top10 clone, CD38-A2 wild type 20170801(R023-32) QAGLT (SEQ ID NO: 4) | ~50% | ~50% | 48% | 48% |
| Top10 clone, CD38-A2 wild type 20170809, (R042-51) QAGLT (SEQ ID NO: 4) | NA | NA | ~50% | ~50% |
| CD38-A2 wild type 20170612_0245-159_CD38 (S)_Pool_20170623 QAGLT (SEQ ID NO: 4) | 56% | 44% | 51% | 49% |
| CD38-A2 wild type 20170418_0245-140_CD38 A2 Stable_20170424 QAGLT (SEQ ID NO: 4) | 39% | 61% | 55% | 45% |
| CD38 A2-SA, 20170818 (R052), QSALT (SEQ ID NO: 6) | ~99% | ~1% | ~100% | Not Detected |
| CD38 A2-SV, 20170818 (R053), QSVLT (SEQ ID NO: 5) | 100% | Not Detected | ~100% | Not Detected |

Figure 3A:
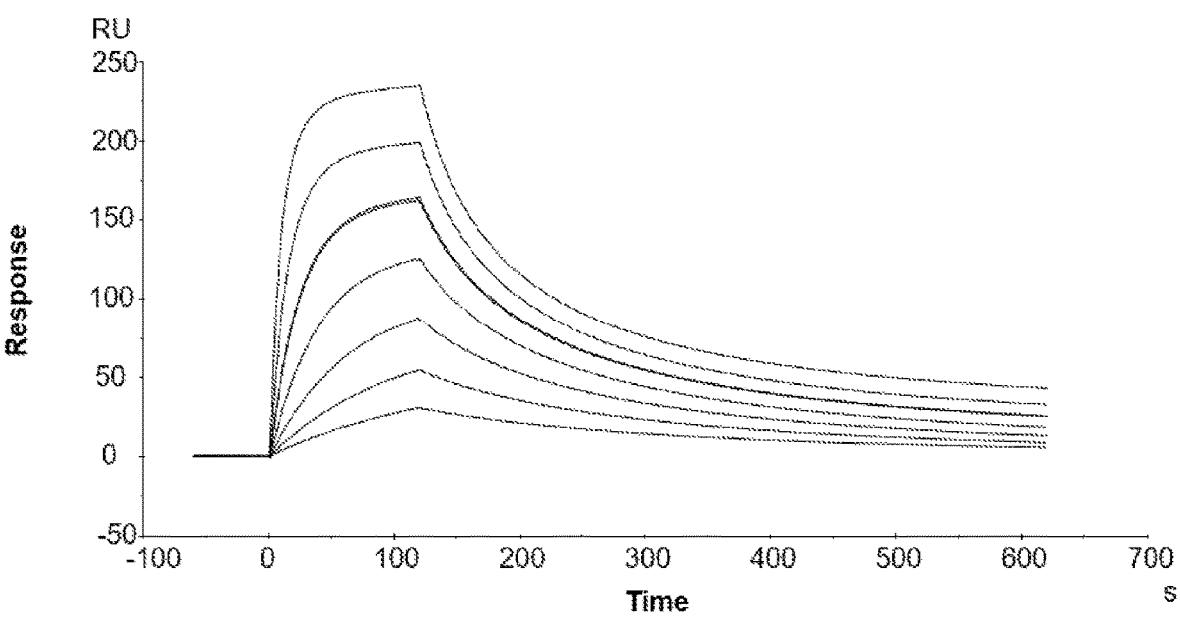
FIG. 3A shows an SPR sensorgram of binding kinetics of parent antibody CD38 A2.
Figure 3B:
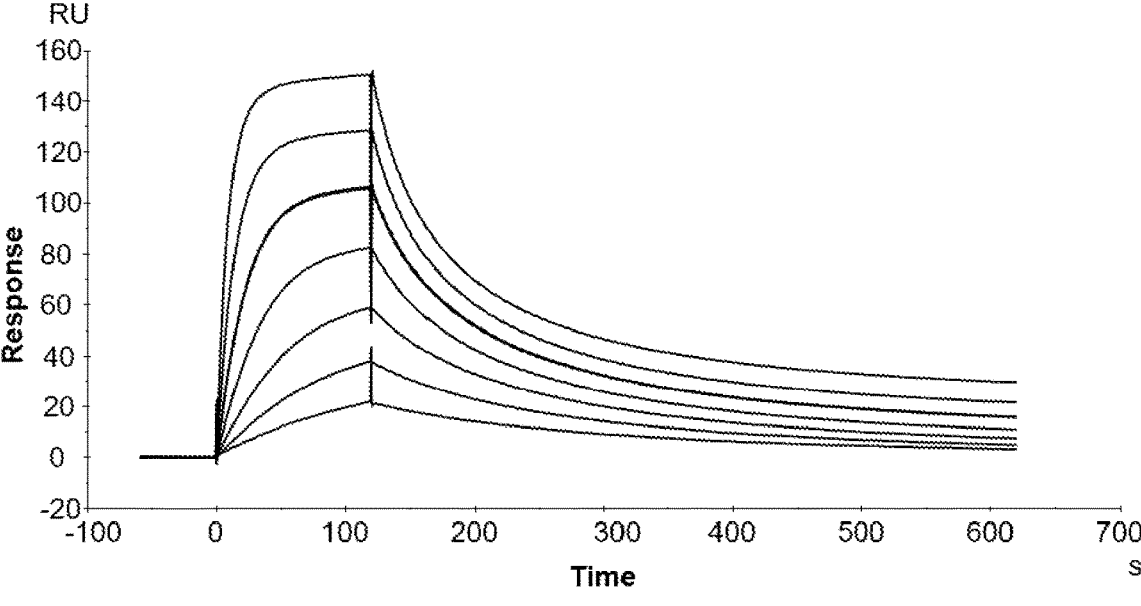
FIG. 3B shows an SPR sensorgram of binding kinetics of variant antibody CD38 A2 SV.

Example 3: Comparative Binding Studies Parent Antibody CD38 A2 and Variant Antibody CD38 A2 SV Binding kinetics of parent antibody CD38 A2 and variant antibody CD38 A2 SV was measured using surface plasmon resonance (SPR). Kinetic interaction between the parent or variant antibody and a his-tagged CD38 protein were measured at 25° C. using Biacore T200 surface plasmon resonance (GE Healthcare). Anti-human fragment crystallizable region (Fc region) antibody was immobilized on a CM5 sensor chip to approximately 8000 resonance units (RU) using standard N hydroxysuccinimide/N Ethyl-N'-(3-dimethylaminopropyl) carbodiimide hydrochloride (NHS/EDC) coupling methodology. The CD38 A2 parent antibody or CD38 A2 SV variant antibody (2 μg/mL) was captured for 60 seconds at a flow rate of 10 μL/minute. Recombinant human his-tagged CD38 protein was serially diluted in a running buffer of 0.01 M HEPES pH 7.4, 0.15 M NaCl, 3 mM EDTA, 0.05% v/v Surfactant P20 (HBS EP+). All measurements were conducted in HBS-EP+ buffer with a flow rate of 30 μL/minute. Steady state affinity model was used to get affinity. The sensorgrams of the CD38 A2 parent antibody and CD38 A2 SV variant antibody are shown in FIGS. 3A and B, respectively, and their corresponding binding kinetics are listed in Table 3 below.

TABLE 3

| | $K_D$ (M) |
|---|---|
| Parent CD38 A2 | $1.63 \times 10^{-8}$ |
| Variant CD38 A2 SV | $1.56 \times 10^{-8}$ |

What is claimed:

1. An antigen binding protein that binds CD38, comprising a heavy chain variable region and a light chain variable region, wherein the heavy chain variable region comprises the sequence of SEQ ID NO: 1 and the light chain variable region comprises the sequence of SEQ ID NO: 3.

2. The antigen binding protein of claim 1, which is a fully human single chain antibody, comprising a heavy chain comprising a heavy chain variable region having the amino acid sequence of SEQ ID NO:1, and a light chain comprising a light chain variable region having the amino acid sequence of SEQ ID NO:3.

3. A pharmaceutical composition comprising a pharmaceutically-acceptable excipient and the antigen binding protein of claim 1.

4. A fully human antibody of an IgG class or antibody Fab fragment thereof, comprising a heavy chain comprising a heavy chain variable region having the amino acid sequence of SEQ ID NO:1, and a light chain comprising a light chain variable region having the amino acid sequence of SEQ ID NO:3.

5. The fully human antibody or antibody Fab fragment thereof of claim 4, which is a fully human antibody.

6. The fully human antibody or antibody Fab fragment thereof of claim 4, which is a Fab fragment.

7. A nucleic acid encoding the fully human antibody of claim 4.

8. A nucleic acid encoding an antibody light chain comprising a light chain variable region having the amino acid sequence of SEQ ID NO:3.

9. The nucleic acid of claim 8, further comprising a nucleic acid encoding an antibody heavy chain which comprises the amino acid sequence of SEQ ID NO:1.

10. An expression vector comprising a promoter operably linked to the nucleic acid of claim 8.

11. The expression vector of claim 10 further comprising a nucleic acid encoding an antibody heavy chain which comprises the amino acid sequence of SEQ ID NO: 1.

12. An isolated host cell comprising the expression vector of claim 11.

13. A method for preparing a fully human antibody light chain, comprising: culturing a population of the host cell of claim 12 under conditions suitable for expressing the antibody light chain.

14. The method of claim 13, further comprising recovering from the host cells the expressed antibody light and heavy chains.

15. The method of claim 14, wherein the percentage of the recovered expressed antibody light chains having the correct length, the correct N-terminal amino acid, and having 100% sequence identity to the light chain variable domain of SEQ ID NO: 3 is 90-100%.

16. An isolated host cell comprising the expression vector of claim 10.

17. A method for preparing a fully human antibody light chain, comprising: culturing a population of the host cell of claim 16 under conditions suitable for expressing the antibody light chain.

18. The method of claim 17, further comprising recovering from the host cells the expressed antibody light chain.

19. The method of claim 18, wherein the percentage of the recovered expressed antibody light chains having the correct length, the correct N-terminal amino acid, and having 100% sequence identity to the light chain variable domain of SEQ ID NO: 3 is 90-100% and/or wherein the homogeneity of the recovered expressed antibody light chains is 90-100%.

\* \* \* \* \*